(12) United States Patent
Fukuzawa et al.

(10) Patent No.: US 11,541,394 B2
(45) Date of Patent: Jan. 3, 2023

(54) REACTION PROCESSOR

(71) Applicants: Nippon Sheet Glass Company, Limited, Tokyo (JP); Go!Foton, Inc., Tsukuba (JP)

(72) Inventors: Takashi Fukuzawa, Tokyo (JP); Naofumi Nishizawa, Ibaraki (JP); Hisao Nagata, Ibaraki (JP)

(73) Assignees: Nippon Sheet Glass Company, Limited, Tokyo (JP); Go!Foton, Inc., Tsukuba (JP)

( * ) Notice: Subject to any disclaimer, the term of this patent is extended or adjusted under 35 U.S.C. 154(b) by 489 days.

(21) Appl. No.: 16/687,804

(22) Filed: Nov. 19, 2019

(65) Prior Publication Data

US 2020/0086313 A1 Mar. 19, 2020

Related U.S. Application Data

(63) Continuation of application No. PCT/JP2018/020471, filed on May 29, 2018.

(30) Foreign Application Priority Data

Jun. 6, 2017 (JP) .............................. JP2017-111817

(51) Int. Cl.
| | | |
|---|---|---|
| B01L 3/00 | (2006.01) | |
| B01J 19/00 | (2006.01) | |
| C12Q 1/6806 | (2018.01) | |
| C12Q 1/686 | (2018.01) | |
| B01L 7/00 | (2006.01) | |
| C12M 1/38 | (2006.01) | |

(52) U.S. Cl.
CPC ........ *B01L 3/50851* (2013.01); *B01J 19/0093* (2013.01); *B01L 3/502715* (2013.01); *B01L 7/525* (2013.01); *C12M 1/38* (2013.01); *C12Q 1/686* (2013.01); *C12Q 1/6806* (2013.01); *B01J 2219/00873* (2013.01); *B01J 2219/00986* (2013.01)

(58) Field of Classification Search
CPC ........... B01L 3/50851; B01L 3/502715; B01L 7/525; B01L 2200/147; B01L 2300/0883; B01J 19/0093; B01J 2219/00873; B01J 2219/00986; C12M 1/38; C12M 1/00; C12Q 1/6806; C12Q 1/686; G01N 35/08; G01N 21/13; G01N 35/00; G01N 37/00; C12N 15/09; C12N 21/64

See application file for complete search history.

(56) References Cited

U.S. PATENT DOCUMENTS

| | | | |
|---|---|---|---|
| 2010/0267017 A1 | 10/2010 | Hassard | |
| 2012/0178091 A1* | 7/2012 | Glezer | .................. B01L 7/525 435/6.12 |
| 2017/0130261 A1* | 5/2017 | Nagai | .................. C12M 1/00 |

FOREIGN PATENT DOCUMENTS

| | | |
|---|---|---|
| EP | 0347579 B1 | 3/1994 |
| JP | 2009-517075 A | 4/2009 |
| JP | 2009-232700 A | 10/2009 |
| JP | 2013-55921 A | 3/2013 |
| WO | 92/13967 A1 | 8/1992 |
| WO | 03/057875 A1 | 7/2003 |
| WO | 2015/119470 A1 | 8/2015 |
| WO | 2016/006612 A1 | 1/2016 |
| WO | 2017/199933 A1 | 11/2017 |

OTHER PUBLICATIONS

Communication dated Feb. 3, 2021, issued by the European Patent Office in counterpart European Application No. 18813162.7.
Chiou et al., "A Closed-Cycle Capillary Polymerase Chain Reaction Machine", Analytical Chemistry, American Chemical Society, vol. 73, No. 9, May 1, 2001, XP001071442, pp. 2018-2021, (4 pages total).
International Search Report dated Aug. 21, 2018 from International Searching Authority in International Application No. PCT/JP2018/020471.
International Preliminary Report on Patentability with the translation of Written Opinion dated Dec. 19, 2019 from International Bureau in International Application No. PCT/JP2018/020471.
Office Action dated Dec. 17, 2021 from the Intellectual Property Office of India in IN Application No. 201917045457.
Communication dated Apr. 13, 2021, issued by the Federal Agency for Intellectual Property in Russian Application No. 2019143829/28.

\* cited by examiner

*Primary Examiner* — Cynthia B Wilder
(74) *Attorney, Agent, or Firm* — Sughrue Mion, PLLC

(57) ABSTRACT

A reaction processor is provided with a reaction processing vessel in which a channel is formed, a liquid feeding system, a temperature control system for providing a high temperature region and a low temperature region to the channel, and a fluorescence detector for detecting the sample passing through a fluorescence detection region of the channel, and a CPU for controlling the liquid feeding system based on a signal that is detected. A target stop position $X^{[L]}_0(n+1)$ of the sample in the low temperature region in an (n+1)th cycle is corrected from a target stop position $X^{[L]}_0(n)$ of the sample in the low temperature region in the nth cycle based on the result of stopping control on the sample in the nth cycle.

6 Claims, 9 Drawing Sheets

REACTION PROCESSOR

BACKGROUND OF THE INVENTION

1. Field of the Invention

The present invention relates to reaction processors used for polymerase chain reactions (PCR).

BACKGROUND ART

Genetic testing is widely used for examinations in a wide variety of medical fields, identification of farm products and pathogenic microorganisms, safety assessment for food products, and even for examinations for pathogenic viruses and a variety of infectious diseases. In order to detect a minute amount of DNA, which is a gene carrier, with high sensitivity, methods of analyzing the resultant obtained by amplifying a portion of DNA are known. Above all, PCR is a remarkable technology where a certain portion of a very small amount of DNA collected from an organism or the like is selectively amplified.

In PCR, a predetermined thermal cycle is applied to a sample in which a biological sample containing DNA and a PCR reagent consisting of primers, enzymes, and the like are mixed so as to cause denaturation, annealing, and elongation reactions to be repeated so that a specific portion of DNA is selectively amplified.

It is a common practice to perform PCR by putting a predetermined amount of a target sample into a PCR tube or a reaction processing vessel such as a microplate (microwell) in which a plurality of holes are formed. However, in recent years, PCR using a reaction processing vessel (also referred to as "chip") provided with a micro-channel that is formed on a substrate is practiced (e.g. Patent Document 1).

[Patent Document 1] Japanese Patent Application Publication No. 2009-232700

SUMMARY OF THE INVENTION

In PCR using a reaction vessel of a reciprocating channel type, in order to apply a thermal cycle to a sample, a plurality of temperature regions each maintained at a different temperature are set on a channel, and the sample is moved in a reciprocating manner between the plurality of temperature regions in the channel. In order to properly apply a thermal cycle to the sample, it is necessary for the sample to stop accurately in each temperature region. Variations in the stop position may prevent reactions from occurring, cause the progress of reactions to vary according to the location of the sample, and cause reactions such as amplification of DNA to be inaccurate, which may lead to erroneous judgment by workers and/or those engaged in the work.

In this background, a purpose of the present invention is to provide a technology capable of precisely stopping a sample at a predetermined position in a temperature region in a reaction processor capable of applying a thermal cycle to the sample by moving the sample in a reciprocating manner in a channel in which different temperature regions are set.

A reaction processor according to an embodiment of the present invention includes: a reaction processing vessel in which a channel where a sample moves is formed; a liquid feeding system that moves and stops the sample in the channel; a temperature control system that provides a plurality of temperature regions each maintained at a different temperature, the plurality of temperature regions including at least a first temperature region and a second temperature region; a detection system that detects the sample passing through a detection region that is set between adjacent temperature regions of the channel, the detection region including at least a first detection region that is set between the first temperature region and the second temperature region of the channel; and a control unit that controls the liquid feeding system based on a signal detected by the detection system. The control unit is formed to perform reciprocation control for a plurality of cycles on the sample where, in one cycle, the sample is stopped for a fixed period of time in the first temperature region, then moves from the first temperature region to the second temperature region after passing through the first detection region and is then stopped for a fixed period of time, and then returns to the first temperature region and then stops. Given that: a waiting time required until the time at which the control unit instructs the liquid feeding system to stop the sample after the time at which the passage of the sample through the first detection region is detected by the detection system with regard to movement from the first temperature region to the second temperature region in an nth cycle (n is an integer of 1 or more) is denoted as $t^{1 \to 2}_p(n)$; a target stop position of the sample in the second temperature region in the nth cycle is denoted as $X^{[2]}_0(n)$; the transit time of the sample through the detection region with regard to the movement from the first temperature region to the second temperature region in the nth cycle is denoted as $t^{1 \to 2}_p(n)$; the length of the sample in the channel is denoted as L; and a fixed period of time specific to the reaction processor is denoted as $t_c$, the waiting time $t^{1 \to 2}_d(n)$ is defined by the following equation: $t^{1 \to 2}_d(n) = X^{[2]}_0(n) * t^{1 \to 2}_p(n)/L - t_c$. A target stop position $X^{[2]}_0(n+1)$ of the sample in the second temperature region in an (n+1)th cycle is corrected from the target stop position $X^{[2]}_0(n)$ of the sample in the second temperature region in the nth cycle based on the result of stopping control on the sample in the nth cycle.

The target stop position $X^{[2]}_0(n+1)$ of the sample in the second temperature region in the (n+1)th cycle may be corrected from the target stop position $X^{[2]}_0(n)$ of the sample in the second temperature region in the nth cycle based on a stop position $X^{[2]}_1(n)$ of the sample in the second temperature region in the nth cycle and a designed target stop position $X^{[2]}_{00}$ in the second temperature region.

The target stop position $X^{[2]}_0(n+1)$ of the sample in the second temperature region in the (n+1)th cycle may be corrected from the target stop position $X^{[2]}_0(n)$ of the sample in the second temperature region in the nth cycle based on the difference $\Delta X^{[2]}(n)$ between the stop position $X^{[2]}_1(n)$ of the sample in the second temperature region in the nth cycle and the designed target stop position $X^{[2]}_{00}$ in the second temperature region.

The target stop position $X^{[2]}_0(n+1)$ of the sample in the second temperature region in the (n+1)th cycle may be determined by correcting the target stop position $X^{[2]}_0(n)$ of the sample in the second temperature region in the nth cycle.

The target stop position $X^{[2]}_0(n+1)$ of the sample in the second temperature region in the (n+1)th cycle may be set by the following equation: $X^2_0(n+1) = X^{[2]}_0(n) + k^{[2]}(n)$, and a correction term $k^{[2]}(n)$ may be determined based on the relationship with the difference $\Delta X^{[2]}(n)$ in the nth cycle.

The correction term $k^{[2]}(n)$ may be determined with reference to a table describing the relationship between the difference $\Delta X^{[2]}(n)$ and the correction term $k^{[2]}(n)$ in the nth cycle.

The stop position $X^{[2]}_1(n)$ of the sample in the second temperature region in the nth cycle may be obtained as $X^{[2]}_{11}(n)$ determined by the following equation: $X^{[2]}_{11}(n)=L/t^{2\to nt}{}_p(n)*\{t^{2\to nt}{}_{mp}(n)-t_c\}$. In this equation, $t^{2\to nt}{}_p(n)$ is the transit time through a detection region through which the sample passes immediately after leaving the second temperature region with regard to movement from the second temperature region to the subsequent temperature region, and $t^{2\to nt}{}_{mp}(n)$ is the time required from when the operation of the liquid feeding system is started in order to move the sample until when the control unit recognizes that the head of the sample has reached the detection region through which the sample passes immediately thereafter with regard to the movement from the second temperature region to the subsequent temperature region.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1A:
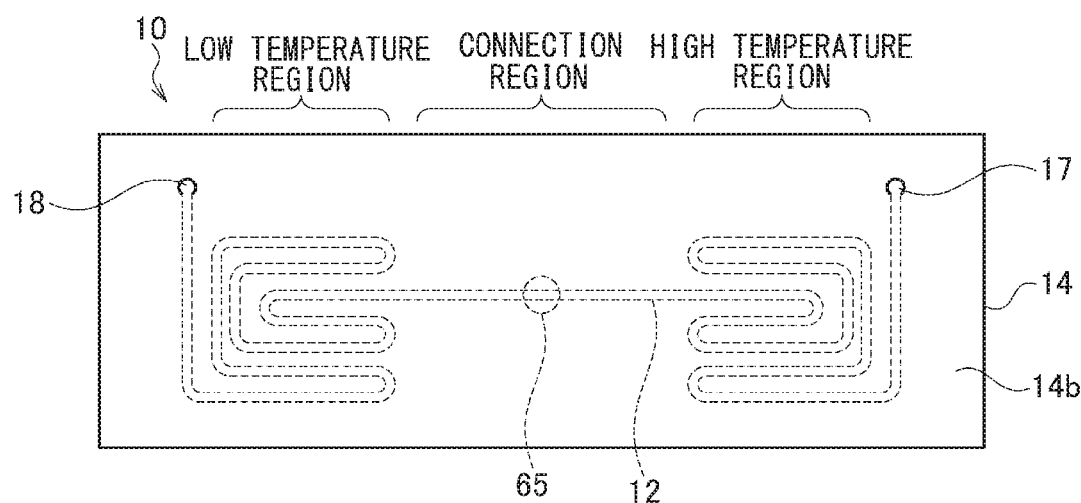
FIGS. 1A and 1B are diagrams for explaining a reaction processing vessel usable in a reaction processor according to an embodiment of the present invention.

An explanation will be given in the following regarding a reaction processor according to an embodiment of the present invention. This reaction processor is a device for performing PCR. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

Figure 1B:
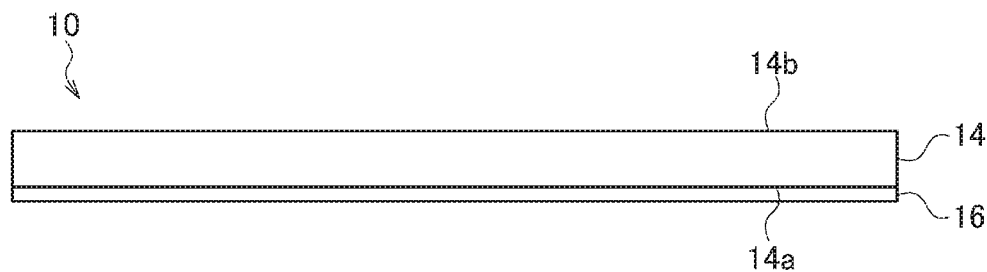

FIGS. 1A and 1B are diagrams for explaining a reaction processing vessel 10 usable in a reaction processor according to an embodiment of the present invention. FIG. 1A is a plan view of the reaction processing vessel 10, and FIG. 1B is a front view of the reaction processing vessel 10.

As shown in FIGS. 1A and 1B, the reaction processing vessel 10 comprises a substrate 14 and a channel sealing film 16.

The substrate 14 is preferably formed of a material that is stable under temperature changes and is resistant to a sample solution that is used. Further, the substrate 14 is preferably formed of a material that has good moldability, a good transparency and barrier property, and a low self-fluorescence property. As such a material, an inorganic material such as glass, silicon (Si), or the like, a resin such as acrylic, polyester, silicone, or the like, and particularly cycloolefin are preferred. An example of the dimensions of the substrate 14 includes a long side of 75 mm, a short side of 25 mm, and a thickness of 4 mm.

A groove-like channel 12 is formed on the lower surface 14a of the substrate 14, and this channel 12 is sealed by the channel sealing film 16. An example of the dimensions of the channel 12 formed on the lower surface 14a of the substrate 14 includes a width of 0.7 mm and a depth of 0.7 mm. A first communication port 17, which communicates with the outside, is formed at the position of one end of the channel 12 in the substrate 14. A second communication port 18 is formed at the position of the other end of the channel 12 in the substrate 14. The pair, the first communication port 17 and the second communication port 18, formed on the respective ends of the channel 12 is formed so as to be exposed on the upper surface 14b of the substrate 14. Such a substrate can be produced by injection molding or cutting work with an NC processing machine or the like.

As shown in FIG. 1B, on the lower surface 14a of the substrate 14, the channel sealing film 16 is attached. In the reaction processing vessel 10 according to the embodiment, most of the channel 12 is formed in the shape of a groove exposed on the lower surface 14a of the substrate 14. This is for allowing for easy molding by injection molding using a metal mold or the like. In order to seal this groove so as to make use of the groove as a channel, the channel sealing film 16 is attached on the lower surface 14a of the substrate 14.

The channel sealing film 16 may be sticky and/or adhesive on one of the main surfaces thereof or may have a functional layer that exhibits stickiness and/or adhesiveness through pressing, energy irradiation with ultraviolet rays or the like, heating, etc., formed on one of the main surfaces. Thus, the channel sealing film 16 has a function of being easily able to become integral with the lower surface 14a of the substrate 14 while being in close contact with the lower surface 14a. The channel sealing film 16 is desirably formed of a material, including an adhesive, that has a low self-fluorescence property. In this respect, a transparent film made of a resin such as cycloolefin, polyester, polypropylene, polyethylene or acrylic is suitable but is not limited thereto. Further, the channel sealing film 16 may be formed of a plate-like glass or resin. Since rigidity can be expected in this case, the channel sealing film 16 is useful for preventing warpage and deformation of the reaction processing vessel 10.

The channel 12 is provided with a reaction region where the control of temperatures of a plurality of levels is possible by a reaction processor described later. A thermal cycle can be applied to a sample by moving the sample such that the sample continuously reciprocates in the reaction region where the temperatures of a plurality of levels are maintained.

The reaction region of the channel 12 shown in FIGS. 1A and 1B includes a serpiginous shape channel with continuous turns made by combining curved portions and straight portions. When the reaction processing vessel 10 is mounted on a reaction processor described later, the right side of the channel 12 in the figures is expected to become a reaction region of a relatively high temperature (about 95° C.) (hereinafter referred to as "high temperature region"), and the left side of the channel 12 is expected to become a region of a lower temperature (about 55° C.) (hereinafter referred to as "low temperature region"). Further, the reaction region of the channel 12 includes a connection region for connecting the high temperature region and the low temperature region therebetween. This connection region may be a linear channel.

When the high temperature region and the low temperature region are serpiginous shape channels as in the present embodiment, the effective area of a heater or the like constituting a temperature control means described later can be effectively used, and there are advantages that temperature variance in the reaction region is easily reduced and that the substantial size of the reaction processing vessel can be reduced, allowing the reaction processor to be made small.

The sample subjected to a thermal cycle is introduced into the channel 12 through either one of the first communication port 17 and the second communication port 18. The method for the introduction is not limited to this. Alternatively, for example, an appropriate amount of the sample may be directly introduced through the communication port using a pipette, a dropper, a syringe, or the like. Alternatively, a method of introduction may be used that is performed while preventing contamination via a cone-shaped needle chip, in which a filter made of porous PTFE or polyethylene is incorporated. In general, many types of such needle chips are sold and can be obtained easily, and the needle chips can be used while being attached to the tip of a pipette, a dropper, a syringe, or the like. Furthermore, the sample may be moved to a predetermined position in the channel by discharging and introducing the sample by a pipette, a dropper, a syringe, or the like and then further pushing the sample through pressurization.

The sample includes, for example, those obtained by adding a fluorescent probe, a thermostable enzyme and four types of deoxyribonucleoside triphosphates (dATP, dCTP, dGTP, dTTP) as PCR reagents to a mixture containing one or more types of DNA. Further, a primer that specifically reacts to DNA subjected to a reaction process is mixed. Commercially available real-time PCR reagent kits and the like can be also used.

Figure 2:
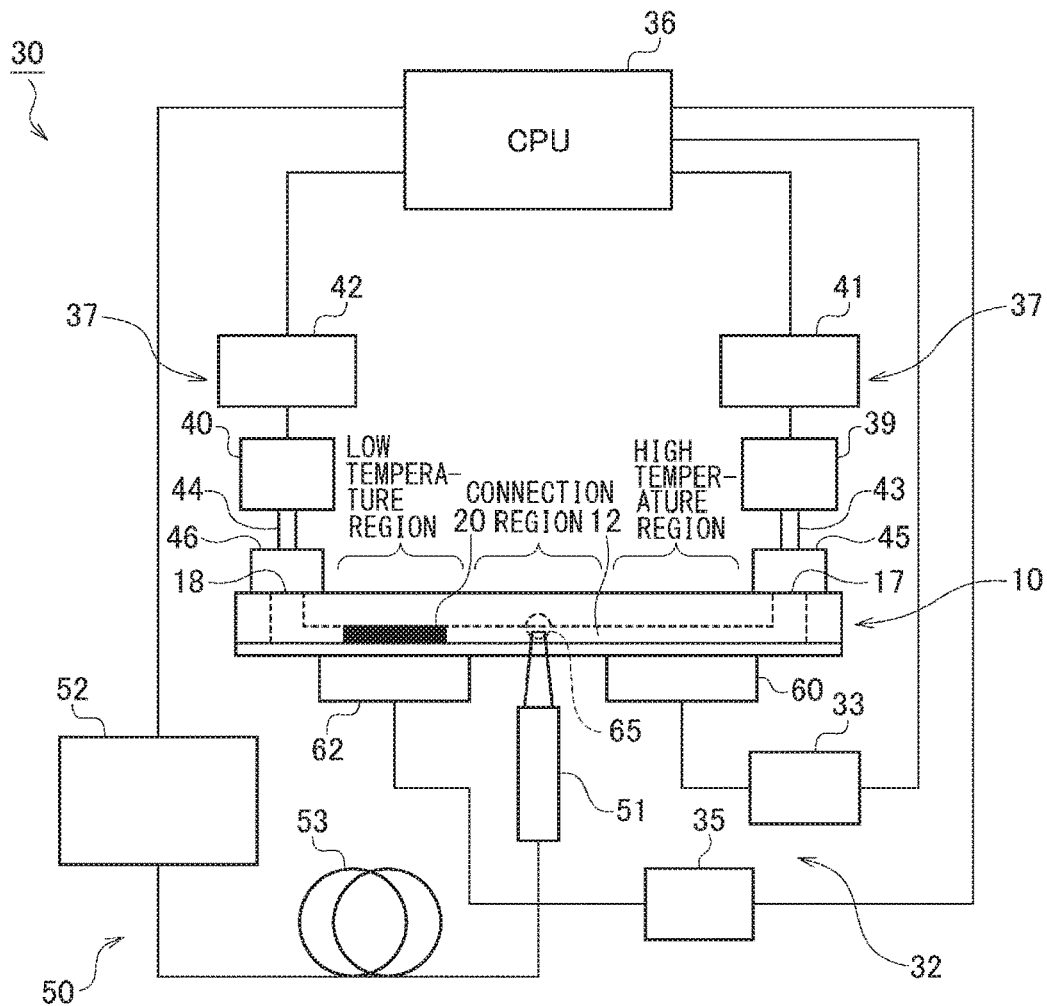
FIG. 2 is a schematic diagram for explaining the reaction processor according to the embodiment of the present invention.

FIG. 2 is a schematic diagram for explaining a reaction processor 30 according to the embodiment of the present invention.

The reaction processor 30 according to the embodiment is provided with a reaction processing vessel placing portion (not shown) on which the reaction processing vessel 10 is placed, a temperature control system 32, and a CPU 36. As shown in FIG. 2, relative to the reaction processing vessel 10 placed on the reaction processing vessel placing portion, the temperature control system 32 is configured so as to be able to accurately maintain and control the temperature of the right side region of the channel 12 of the reaction processing vessel 10 in the figure to be about 95° C. (high temperature range) and the temperature of the left side region thereof in the figure to be about 55° C. (low temperature range).

The temperature control system 32 is for maintaining the temperature of each temperature region of the reaction region and is specifically provided with a high temperature heater 60 for heating the high temperature region of the channel 12, a low temperature heater 62 for heating the low temperature region of the channel 12, a temperature sensor (not shown) such as, for example, a thermocouple or the like for measuring the actual temperature of each temperature region, a high temperature heater driver 33 for controlling the temperature of the high temperature heater 60, and a low temperature heater driver 35 for controlling the temperature of the low temperature heater 62. Information on the actual temperature measured by the temperature sensor is sent to the CPU 36. Based on the information on the actual temperature of each temperature region, the CPU 36 controls each heater driver such that the temperature of each heater becomes a predetermined temperature. Each heater may be, for example, a resistance heating element, a Peltier element, or the like. The temperature control system 32 may be further provided with other components for improving the temperature controllability of each temperature region.

The reaction processor 30 according to the present embodiment is further provided with a liquid feeding system 37 for moving, inside the channel 12, the sample 20 introduced into the channel 12 of the reaction processing vessel 10. The liquid feeding system 37 is provided with a first pump 39, a second pump 40, a first pump driver 41 for driving the first pump 39, a second pump driver 42 for driving the second pump 40, a first tube 43, and a second tube 44.

One end of the first tube 43 is connected to the first communication port 17 of the reaction processing vessel 10. A packing material 45 or a seal for securing airtightness is preferably arranged at the junction of the first communication port 17 and the end of the first tube 43. The other end of the first tube 43 is connected to the output of the first pump 39. In the same way, one end of the second tube 44 is connected to the second communication port 18 of the reaction processing vessel 10. A packing material 46 or a seal for securing airtightness is preferably arranged at the junction of the second communication port 18 and the end of the second tube 44. The other end of the second tube 44 is connected to the output of the second pump 40.

The first pump 39 and the second pump 40 may be, for example, micro blower pumps each comprising a diaphragm pump. As the first pump 39 and the second pump 40, for example, micro blower pumps (MZB1001 T02 model) manufactured by Murata Manufacturing Co., Ltd., or the like can be used. While this micro blower pump can increase the pressure on a secondary side to be higher than a primary side during operation, the pressure on the primary side and the pressure on the secondary side become equal at the moment when the pump is stopped or when the pump is stopped.

The CPU 36 controls the air supply and pressurization from the first pump 39 and the second pump 40 via the first pump driver 41 and the second pump driver 42. The air supply and pressurization from the first pump 39 and the second pump 40 act on the sample 20 inside the channel through the first communication port 17 and the second communication port 18 and becomes a propulsive force to move the sample 20. More specifically, by alternately operating the first pump 39 and the second pump 40, the pressure applied to either end surface of the sample 20 becomes larger than the pressure applied to the other end, and a propulsive force relating to the movement of the sample 20 can thus be obtained. By alternately operating the first pump 39 and the second pump 40, the sample 20 can be moved in a reciprocating manner in the channel so as to pass through each temperature region of the channel 12 of the reaction processing vessel 10. As a result, a thermal cycle can be applied to the sample 20. More specifically, target DNA in the sample 20 is selectively amplified by repeatedly applying a step of denaturation in the high temperature region and a step of annealing and elongation in the low temperature region. In other words, the high temperature region can be considered to be a denaturation temperature region, and the low temperature region can be considered to be an annealing and elongation temperature region. The time for staying in each temperature region can be appropriately set by changing the time during which the sample 20 stops at a predetermined position in each temperature region.

The reaction processor 30 according to the embodiment is further provided with a fluorescence detector 50. As described above, a predetermined fluorescent probe is added to the sample 20. Since the intensity of a fluorescence signal emitted from the sample 20 increases as the amplification of the DNA proceeds, the intensity value of the fluorescence signal can be used as an index serving as a decision-making factor for the progress of the PCR or the termination of the reaction.

As the fluorescence detector 50, an optical fiber-type fluorescence detector FLE-510 manufactured by Nippon Sheet Glass Co., Ltd., can be used, which is a very compact optical system that allows for rapid measurement and the detection of fluorescence regardless of whether the place is a lighted place or a dark place. This optical fiber-type fluorescence detector allows the wavelength characteristic of the excitation light/fluorescence to be tuned such that the wavelength characteristic is suitable for the characteristic of fluorescence emitted from the sample 20 and thus allows an optimum optical and detection system for a sample having various characteristics to be provided. Further, the optical fiber-type fluorescence detector is suitable for detecting fluorescence from a sample existing in a small or narrow region such as a channel because of the small diameter of a ray of light brought by the optical fiber-type fluorescence detector.

The optical fiber-type fluorescence detector 50 is provided with an optical head 51, a fluorescence detector driver 52, and an optical fiber 53 connecting the optical head 51 and the fluorescence detector driver 52. The fluorescence detector driver 52 includes a light source for excitation light (LED, a laser, or a light source adjusted to emit other specific wavelengths), an optical fiber-type multiplexer/demultiplexer and a photoelectric conversion device (PD, APD, or a light detector such as a photomultiplier) (neither of which is shown), and the like and is formed of a driver or the like for controlling these. The optical head 51 is formed of an optical system such as a lens and has a function of directionally irradiating the sample with excitation light and collecting fluorescence emitted from the sample. The collected fluorescence is separated from the excitation light by the optical fiber-type multiplexer/demultiplexer inside the fluorescence detector driver 52 through the optical fiber 53 and converted into an electric signal by the photoelectric conversion element.

In the reaction processor 30 according to the present embodiment, the optical head 51 is arranged such that fluorescence from the sample 20 passing through a partial region 65 (referred to as "fluorescence detection region 65") inside the connection region connecting the high temperature region and the low temperature region can be detected. Since the reaction progresses while the sample 20 is repeatedly moved in a reciprocating manner in the channel such that predetermined DNA contained in the sample 20 is amplified, by monitoring a change in the amount of detected fluorescence, the progress of the DNA amplification can be learned in real time. Further, in the reaction processor 30 according to the embodiment, an output value from the fluorescence detector 50 is utilized for controlling the movement of the sample 20, as described later. The fluorescence detector is not limited to an optical fiber-type fluorescence detector as long as the fluorescence detector exhibits the function of detecting fluorescence from a sample.

Figure 3:
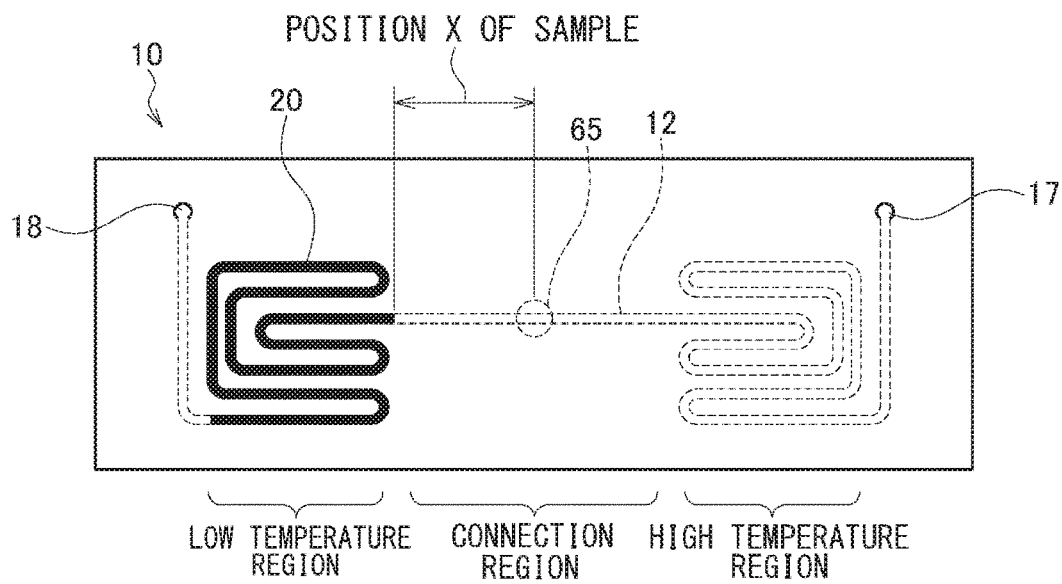
FIG. 3 is a diagram for explaining the stop position of a sample.

FIG. 3 is a diagram for explaining the stop position of a sample. As described above, in the reaction processor 30 according to the embodiment, in order to apply a thermal cycle to the sample 20 by moving the sample in a reciprocating manner in the channel 12, a plurality of temperature regions (i.e., the high temperature region and the lower temperature region) each maintained at a different temperature are set on the channel 12. In order to properly apply a thermal cycle to the sample 20, it is necessary for the sample 20 to stop accurately in each temperature region. Variations in the stop position may prevent reactions from occurring, cause reactions to vary according to the location of the sample, and cause reactions such as amplification of DNA to be inaccurate, which may lead to erroneous judgment by workers and/or those engaged in the work.

As described above, the optical head 51 of the fluorescence detector 50 is provided so as to detect fluorescence from the sample 20 passing through the fluorescence detection region 65 of the channel 12. The fluorescence detector 50 detects a fluorescence signal from the sample 20 in the fluorescence detection region 65 and transmits the signal to the CPU 36 every 0.01 second. The CPU 36 receives the fluorescence signal, performs arithmetic processing such as smoothing of the fluorescence signal value and averaging such as moving average, comparison with a predetermined threshold value (hereinafter sometimes collectively referred to as "evaluation and the like"), and the like, and provides a stop or operation signal to the liquid feeding system 37 based on the result thereof.

In FIG. 3, the fluorescence detection region 65 is arranged close to the middle part between the high temperature region and the low temperature region; however, this is non-limiting. For example, the arrangement thereof may be biased toward the high temperature region side or the low temperature region side. Since the output of the low temperature heater 62 arranged in the low temperature region may be lower than that of the high temperature heater 60 arranged in the high temperature region, it is possible to use heater parts that are accordingly small or thin, and in that case, the optical head 51 can be also arranged while being biased toward the low temperature region.

FIG. 3 shows a condition where the sample 20 is at a position X. The distance X of the sample 20 is the distance between an interface belonging to the end portion of the sample 20 that is closest to the fluorescence detection region 65 and the center of the fluorescence detection region 65. The position of the sample 20 is expressed using a distance X from the center of the fluorescence detection region 65 and is sometimes simply expressed as "position X". Further, even when the sample is in either the high temperature region or the low temperature region, the value of X is assumed to be a scalar distance from the center of the fluorescence detection region 65.

Stopping the sample 20 at a target stop position $X_0$ is now considered. When the sample 20 is present at this target stop position $X_0$, the sample 20 is most appropriately heated and maintained at a predetermined temperature. The target stop position $X_0$ is determined based on the range and position of the temperature region of the processor and the configuration of the reaction processing vessel 10.

As described above, in the case, e.g., where the position of the fluorescence detection region 65 is biased toward either the high temperature region or the low temperature region, the target stop position on the high temperature region side and the target stop position on the low temperature region side are different. Hereinafter, in general, in a case where the target stop position is considered, the distance is simply described as $X_0$. However, it is to be noted that, as described above, the target stop position on the high temperature region side and the target stop position on the low temperature region side do not need to be the same.

The flow for stopping the sample 20 is shown below.

(1) The sample 20 passes through the fluorescence detection region 65 (the fluorescence detector 50 transmits a fluorescence signal to the CPU 36).

(2) The CPU 36 detects the passage of the sample 20 based on the fluorescence signal from the fluorescence detector 50.

(3) The CPU 36 transmits a stop signal for the first pump 39 to the first pump driver 41 or transmits a stop signal for the second pump 40 to the second pump driver 42.

(4) The first pump 39 or the second pump 40 stops.

(5) Sample 20 stops.

In the reaction processing vessel 10 according to the present embodiment, the optical head 51 of the fluorescence detector 50 is disposed near the middle part between the high temperature region and the low temperature region and detects the passage of the sample. Therefore, in order to stop the sample 20 at the target stop position $X_0$, it is necessary to determine how long it should take until the driving of the pump is stopped after the sample 20 passes through the fluorescence detection region 65.

Time (hereinafter, referred to as "waiting time") $t_d$ spent from the time when the passage of the sample 20 through the fluorescence detection region 65 is detected by the fluorescence detector 50 until the time when the CPU 36 instructs the pump to stop the sample 20 via the pump driver can be expressed by the following equation (1).

$$t_d = X_0/v - t_c \quad (1)$$

In equation (1), $X_0$ is a target stop position, v is a moving speed when the sample 20 passes through the fluorescence detecting region 65, and $t_c$ is a constant delay time specific to the processor.

An explanation is given regarding the delay time $t_c$. The passage of the sample 20 is not recognized by the CPU 36 at the same time as the passage is detected by the fluorescence detector 50. A detected fluorescence signal from the sample 20 requires averaging processing of the signal, arithmetic processing for comparison with a threshold value (a reference value of fluorescence signal intensity predetermined in order to judge that the sample 20 exists in the fluorescence detection region 65) for determination, and the like. Therefore, after the sample 20 actually passes through the fluorescence detection region 65, a predetermined delay time $t_c$ is generated until the CPU 36 recognizes the passage.

Figure 4:
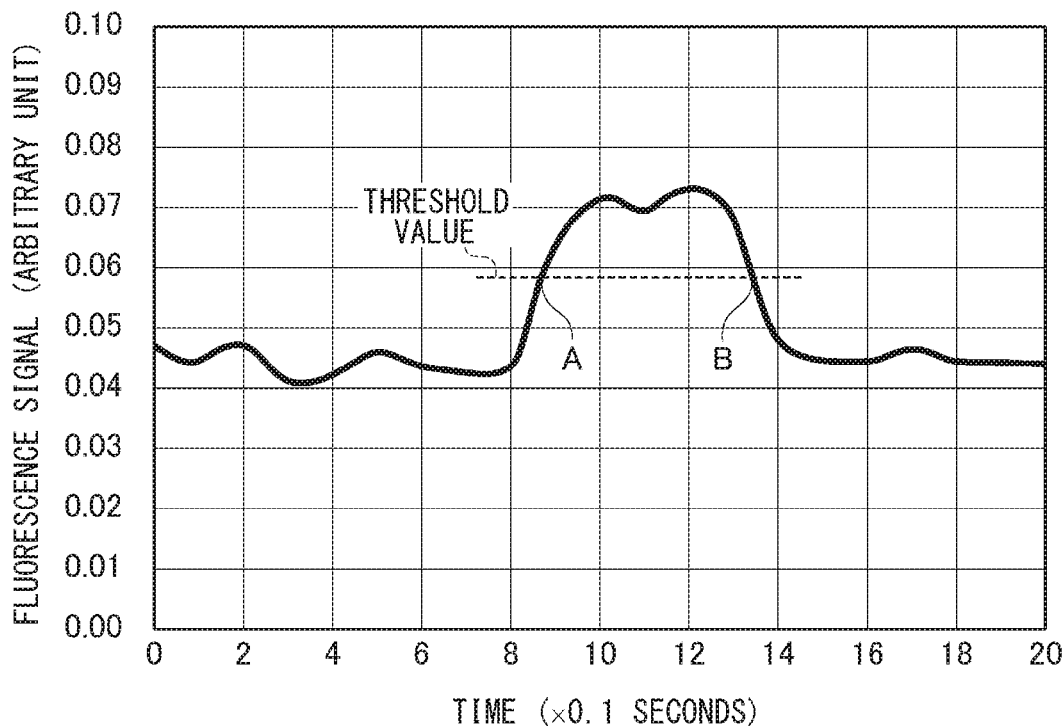
FIG. 4 is a diagram showing changes in a fluorescence signal.

Next, the moving speed v of the sample will be explained. FIG. 4 shows an example of changes in a fluorescence signal detected by the fluorescence detector 50 and obtained as a result of an operation such as moving averaging processing by the CPU 36. In FIG. 4, the horizontal axis shows time having 0 for the time before the sample 20 enters the fluorescence detection region 65 and when the detection of a fluorescence signal is started, and the vertical axis shows the intensity of the fluorescence signal output from the fluorescence detector driver 52. As shown in FIG. 4, when the sample 20 passes through the fluorescence detection region 65, the relationship between the time and the fluorescence signal that is detected is such that the fluorescence signal increases from zero or a baseline as the sample 20 enters the fluorescence detection region 65 and the fluorescence signal drops to zero or the baseline again as the sample 20 exits the fluorescence detection region 65.

Based on the graph shown in FIG. 4, transit time $t_p$ of the sample 20 passing through the fluorescence detection region 65 is obtained. Since the transit time $t_p$ is a difference in time, the transit time is not affected by the delay time of the processor. For example, 50% of the difference between the baseline and the peak value is set as a threshold value, the time corresponding to a point A in FIG. 4 that corresponds to the earliest time is set as entry time of (the leading end part of) the sample 20 and the time corresponding to a point B that corresponds to the latest time is set as exit time of (the rear end part of) the sample 20 among intersection points of a straight line representing a threshold value that is parallel to the horizontal axis and a fluorescence signal curve, and a difference between the time corresponding to the point A and the time corresponding to the point B is set as the transit time $t_p$ of the sample 20. Those skilled in the art can arbitrarily and freely set the percentage of the difference between the peak value of the fluorescence signal and the baseline for the threshold value. Based on the volume of the sample 20 introduced into the channel, the length L of the sample in the channel is determined. Based on the known length L of the sample 20 and the transit time $t_p$ of the sample 20, the CPU 36 can calculate the moving speed v of the sample 20 using $v = L/t_p$.

The delay time $t_c$ can be experimentally obtained by setting a temporary waiting time $t_d$ (may be 0 (seconds) at first) using the target stop position $X_0$ and the moving speed v of the sample, moving the sample 20 in a reciprocating manner, and then obtaining the difference between the actual stop position $X_1$ and the target stop position $X_0$ of the sample 20, followed by performing trial and error for minimizing the difference as much as possible.

The inventors of the present invention introduced an FITC solution (fluorescein isothiocyanate: sample that emits fluorescence) of a predetermined concentration (for example, 100 nM (unit [nM] is nanomolar and is nanomol/liter)) adjusted such that the length thereof in the channel was 40 mm into the channel 12 having a width of 0.7 mm and a depth of 0.7 mm of the reaction processing vessel 10 shown in FIGS. 1A and 1B, and obtained the delay time $t_c$ experimentally based on the predetermined target stop position $X_0$ and the moving speed v (transit time $t_p$) of the sample 20. With regard to the transit time $t_p$ of the sample 20, the output of the pump serving as the thrust of the sample 20 was adjusted so as to become substantially constant (specifically, 0.5 seconds) by predetermined feedback. As a result, in the reaction processing vessel 10 and the reaction processor 30 used in the experiment, by setting the delay time $t_c$ to 0.175 seconds, the difference between the actual stop position $X_1$ and the target stop position $X_0$ of the sample 20 was found to be able to be minimized.

Next, the present inventors used as a sample a reaction solution composition of SpeedSTAR HS DNA Polymerase (SpeedSTAR is a registered trademark) manufactured by TakaraBio Inc., serving as a DNA polymerase for a PCR reagent. This SpeedSTAR HS DNA Polymerase was accompanied by compounds necessary for PCR such as a mixture of the aforementioned deoxyribonucleoside triphosphates (dATP, dCTP, dGTP, dTTP), buffer, etc., and the compounds were prepared as described in a manual so as to be used as the sample. As a result of this, the difference between the actual stop position $X_1$ and the target stop position $X_0$ of the sample was found to become larger gradually when the movement of the sample was controlled based on the above equation (1) in the reaction processor 30. When the actual stop position $X_1$ and the target stop position $X_0$ of the sample becomes large, there is a possibility that the temperature control of the sample cannot be performed with high accuracy.

The present inventors prepared two batches by preparing a sample in which the above-described SpeedSTAR HS DNA Polymerase was made into a reaction solution composition and conducted an experiment for controlling the movement of the sample. Experimental results on these two batches are shown in FIGS. 5 and 6 as Comparative Examples 1 and 2, respectively.

Figure 5:
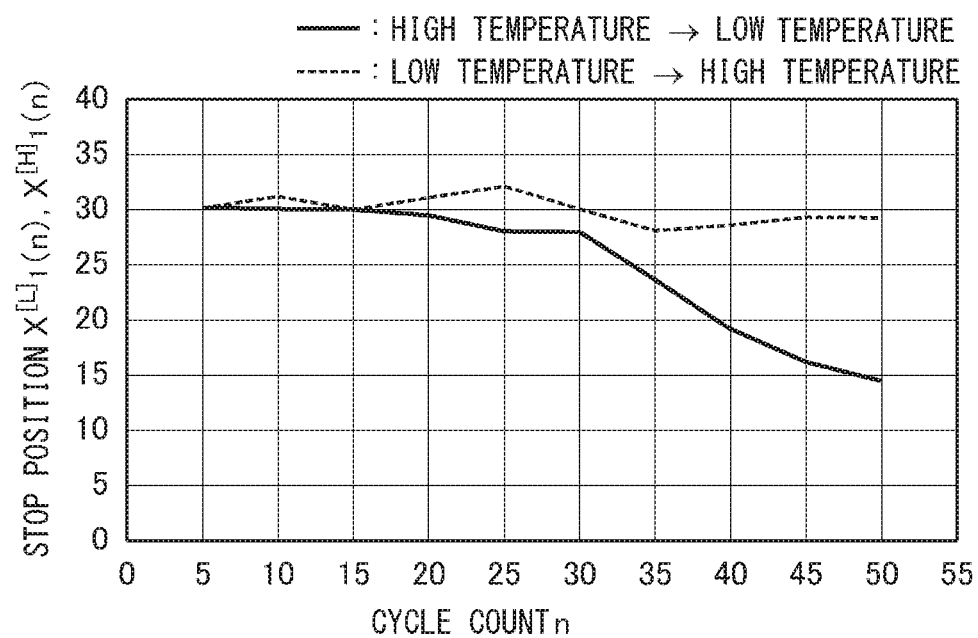
FIG. 5 is a diagram showing the result of an experiment of controlling the movement of a sample according to comparative example 1.
Figure 6:
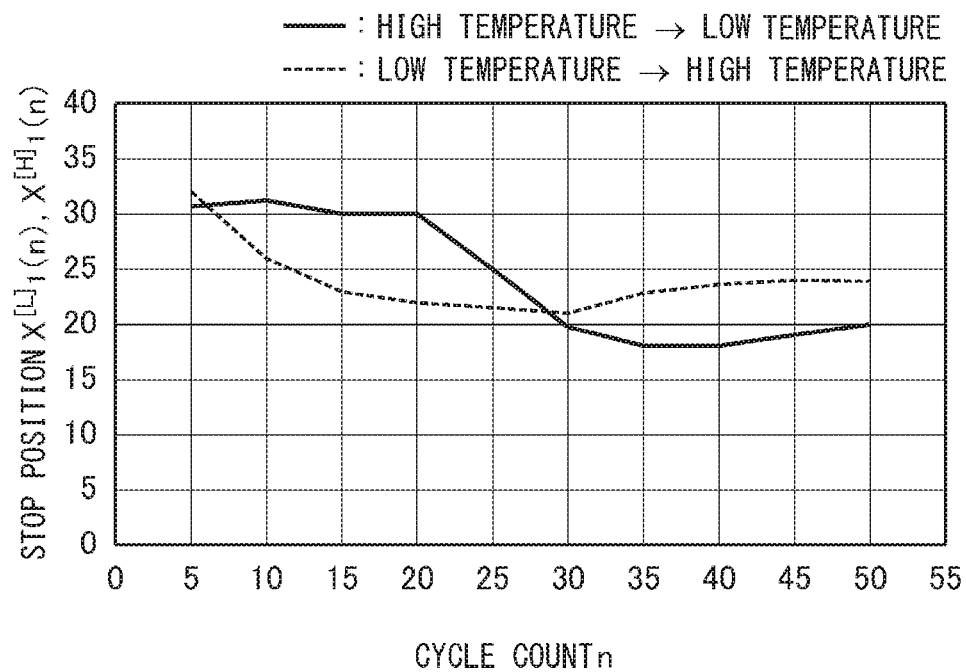
FIG. 6 is a diagram showing the result of an experiment of controlling the movement of a sample according to comparative example 2.

In FIGS. 5 and 6, the horizontal axis represents a cycle count n (n is an integer of 1 or more), and the vertical axis represents the actual stop position $X_1(n)$ corresponding to the cycle count n. In one cycle, the sample moves from a high temperature region to a low temperature region and then returns from the low temperature region to the high temperature region. In FIGS. 5 and 6, the solid line indicates a position $X^{[L]}_1(n)$ at which the sample stopped in the low temperature region when moving from the high temperature region to the low temperature region (H→L), and the broken line indicates a position $X^{[H]}_1(n)$ at which the sample stopped in the high temperature region when moving from the low temperature region to the high temperature region (L→H).

The actual stop positions $X^{[L]}_1(n)$ and $X^{[H]}_1(n)$ of the sample were obtained by actually reciprocating the sample repeatedly, enlarging and observing the sample at a predetermined magnification from directly above, and measuring the distance from the center of the fluorescence detection region 65 to an end of the sample that is close to the fluorescence detection region 65 with a ruler.

As can be seen in FIGS. 5 and 6, the actual stop positions $X^{[L]}_1(n)$ and $X^{[H]}_1(n)$ of the sample tend to decrease as the cycle count n increases, and the tendency is notably apparent in $X^{[L]}_1(n)$ in particular (that is, the sample tends to approach the fluorescence detection region 65 as the cycle count n increases) Since such a phenomenon did not occur even when a sample based only on the FITC solution was introduced, the present inventors found, as a result of an earnest trial and error, that such a phenomenon was caused due to the presence of a surfactant contained in the DNA polymerase in a predetermined amount. In each of the DNA polymerases used in Comparative Examples 1 and 2 shown in FIG. 5 and FIG. 6, Tween20 and Nonidet P-40 (Nonidet is registered trademark), which are nonionic surfactants, were added each in an amount of 0.01 percent by weight.

Figure 7:
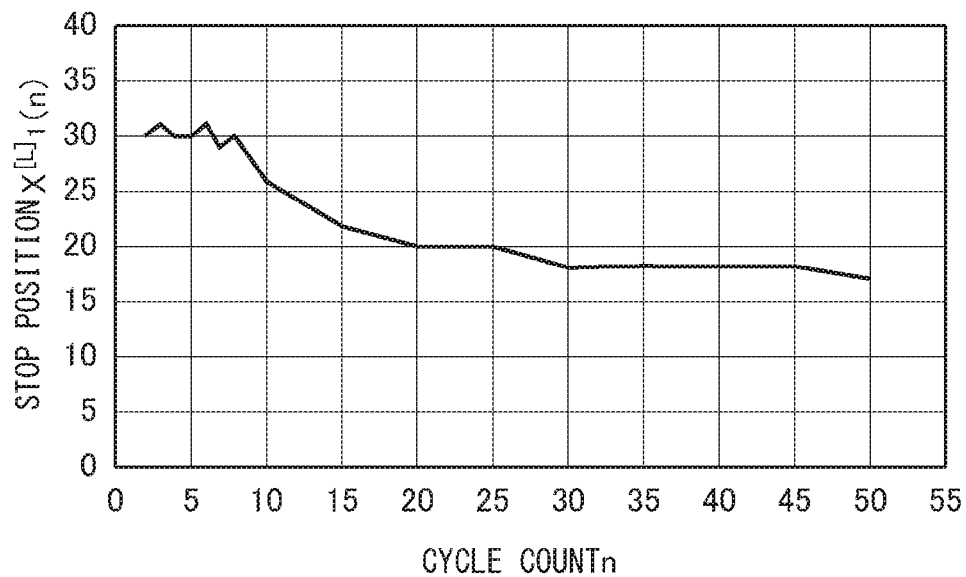
FIG. 7 is a diagram showing the result of an experiment of controlling the movement of a sample according to comparative example 3.

Indeed, a sample was prepared by adding Tween20, which was a surfactant contained in the above DNA polymerases, in an FITC solution of a concentration of 100 nM such that the concentration of Tween20 was 0.01 percent by weight, and the experiment was performed for this sample. The actual stop positions $X^{[L]}_1(n)$ and $X^{[H]}_1(n)$ of the sample had a tendency to decrease as the cycle count n increased, and particularly the tendency was notable in the stop position $X^{[L]}_1(n)$ in the low temperature region when the sample moved from the high temperature region to the low temperature region (H→L). This experimental result is shown in FIG. 7 as Comparative Example 3.

The present inventors made an improvement on a method of controlling the movement of a sample based on the equation (1) in consideration of a situation where such shifting of the sample in the stop position (decrease in a stopping distance) occurred.

An explanation will be given in the following regarding a method of controlling the movement according to the present embodiment. A case where the sample moves from the high temperature region to the low temperature region (H→L) will be considered here. However, it can be considered that the same applies to a case where the sample moves from the low temperature region to the high temperature region (L→H).

First, the above equation (1) for obtaining the waiting time is rewritten to be the following equation (2) using suffixes.

$$t_d^{H \to L}(n) = X_0^{[L]}(n) / v_p^{H \to L}(n) - t_c \qquad (2)$$
$$= X_0^{[L]}(n) * t_p^{H \to L}(n) / L - t_c$$

Figure 8:
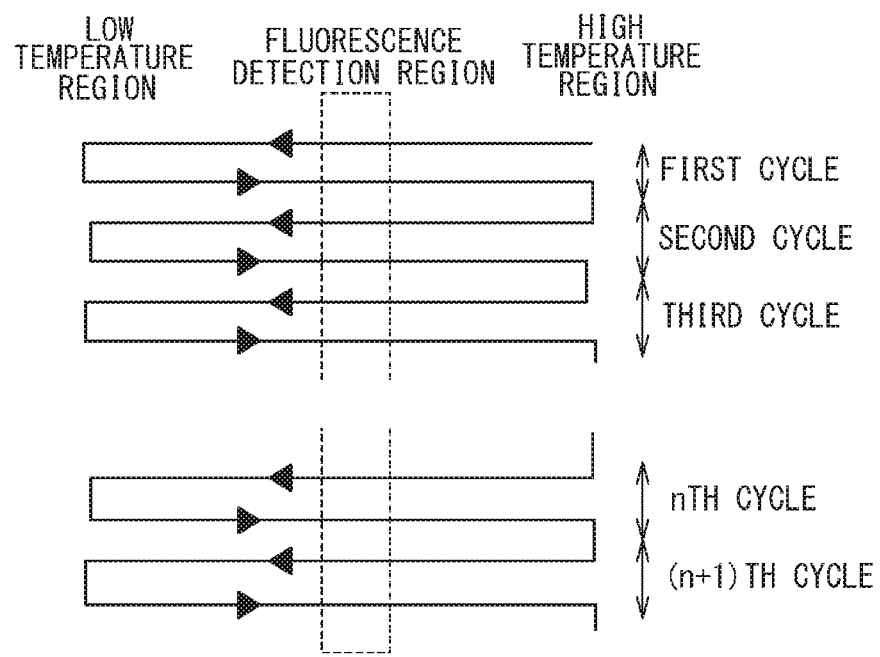
FIG. 8 is a diagram for explaining thermal cycles.

FIG. 8 is a diagram for explaining thermal cycles.

As shown in FIG. 8, in one cycle, the sample moves from a high temperature region to a low temperature region and stops and then returns from the low temperature region to the high temperature region and stops. The CPU 36 of the reaction processor 30 is formed so as to perform reciprocation control for a plurality of cycles on the sample.

A detailed explanation will be given regarding each item in the above equation (2). In the following explanation, n is an integer of 1 or more, and the suffix H→L of each symbol represents the movement from a high temperature region to a low temperature region.

The item $t_d^{H \to L}(n)$ represents a waiting time when the sample moves from the high temperature region to the low temperature region in an nth cycle and is the time required from the time when the passage of the sample through the fluorescence detection region 65 is detected by the fluorescence detector 50 until the time when the CPU 36 instructs the liquid feeding system 37 to stop the sample.

The item $X_0^{[L]}(n)$ is the target stop position of the sample in the low temperature region in the nth cycle and is represented by the distance from the center of the fluorescence detection region 65 to the end of the sample (see FIG. 3).

The item $t^{H \to L}{}_p(n)$ represents the transit time of the sample through the fluorescence detection region 65 with regard to the movement from the high temperature region to the low temperature region in the nth cycle (see FIG. 4). The item $V^{H \to L}{}_p(n)$ represents the moving speed of the sample through the fluorescence detection region 65 with regard to the movement from the high temperature region to the low temperature region in the nth cycle.

L represents the length of the sample in the channel. $t_c$ is a delay time and is an intrinsic constant based on specifications of the reaction processor 30, the reaction processing vessel 10, and the like. The delay time $t_c$=0.175 seconds experimentally obtained as described above was adopted here.

In the reaction processor 30, when moving the sample from the high temperature region to the low temperature region in the nth cycle, the CPU 36 instructs the liquid feeding system 37 to stop the sample at the time when the waiting time $t^{H \to L}{}_d(n)$ defined in the above equation (2) has passed since the time when the passage of the sample through the fluorescence detection region 65 is detected by the fluorescence detector 50.

Here, in the reaction processor 30 according to the present embodiment, a target stop position $X^{[L]}{}_0(n+1)$ of the sample when moving from the high temperature region to the low temperature region in an (n+1)th cycle, which is the subsequent cycle of the nth cycle, is corrected from the target stop position $X^{[L]}{}_0(n)$ of the sample in the nth cycle based on the result of stopping control on the sample in the nth cycle. As shown in FIGS. 5 to 7, there is a tendency that the actual stop position $X^{[L]}{}_1(n)$ of the sample changes (mainly approaches the fluorescence detection region 65) as the cycle count increases when a surfactant is included in the sample. Therefore, by setting the target stop position $X^{[L]}{}_0(n+1)$ of the subsequent (n+1)th cycle based on the result of the stopping control of the sample in the nth cycle, it is possible to stop the sample at a more accurate position. It should be noted that the target stop position $X^{[L]}{}_0(n+1)$ in the (n+1)th cycle can have not only a value that is different from that of the target stop position $X^{[L]}{}_0(n)$ in the nth cycle but also a value that is the same as that of the target stop position $X^{[L]}{}_0(n)$ in the nth cycle as the result of the correction.

More specifically, the target stop position $X^{[L]}{}_0(n+1)$ of the sample in the (n+1)th cycle is corrected from the target stop position $X^{[L]}{}_0(n)$ in the nth cycle based on a difference $\Delta X^{[L]}(n)$ between the actual stop position $X^{[L]}{}_1(n)$ of the sample in the nth cycle and a designed target stop position $X^{[L]}{}_{00}$. The designed target stop position $X^{[L]}{}_{00}$ is a position where the sample should be present in the low temperature region in design. The designed target stop position $X^{[L]}{}_{00}$ is a value that is determined based on the designs and configurations of the reaction processor 30 and the reaction processing vessel 10. It is needless to say that the closer to the designed target stop position $X^{[L]}{}_{00}$ the actual stop position $X^{[L]}{}_1(n)$ of the sample is, the more desirable the actual stop position $X^{[L]}{}_1(n)$ is.

The target stop position $X^{[L]}{}_0(n+1)$ of the sample in the (n+1)th cycle may be set by adding a correction term $k^{[L]}(n)$ to the target stop position $X^{[L]}{}_0(n)$ of the sample in the nth cycle as shown in the following equation (3). The initial value of the correction term $k^{[L]}(n)$ may be 0.

$$X^{[L]}{}_0(n+1) = X^{[L]}{}_0(n) + k^{[L]}(n) \quad (3)$$

The correction term $k^{[L]}(n)$ may be determined based on the difference $\Delta X^{[L]}(n)$ between the actual stop position $X^{[L]}{}_1(n)$ of the sample in the nth cycle and the designed target stop position $X^{[L]}{}_{00}$. For example, a table in which the relationship between the difference $\Delta X^{[L]}(n)$ in the nth cycle and the correction term $k^{[L]}(n)$ is described as shown in the following Table 1 may be prepared in advance, and the correction term $k^{[L]}(n)$ may be determined in reference to the table.

TABLE 1

| $\Delta X^{[L]}(n)$ [unit: mm] | $k^{[L]}(n)$ [unit: mm] |
|---|---|
| $-99 \leq \Delta X^{[L]}(n) < -10$ | +10 |
| $-10 \leq \Delta X^{[L]}(n) < -5$ | +5 |
| $-5 \leq \Delta X^{[L]}(n) \leq 5$ | 0 |
| $5 < \Delta X^{[L]}(n) \leq 10$ | −5 |
| $10 < \Delta X^{[L]}(n) \leq 99$ | −10 |

The above Table 1 defines the following: In the following description, the expression "farther than a certain position X" means "further away from the position X viewed from the fluorescence detection region 65" and means that the value of X representing the position is made larger, and the expression "closer than a certain position X" means "closer than the position X viewed from the fluorescence detection region 65" and means that the value of X representing the position is made smaller.

When the actual stop position $X^{[L]}{}_1(n)$ in the nth cycle is closer than the designed target stop position $X^{[L]}{}_{00}$, the target stop position $X^{[L]}{}_0(n+1)$ in the (n+1)th cycle is set to be farther than the target stop position $X^{[L]}{}_0(n)$ in the nth cycle.

When the actual stop position $X^{[L]}{}_1(n)$ in the nth cycle is almost the same as the designed target stop position $X^{[L]}{}_{00}$, the target stop position $X^{[L]}{}_0(n+1)$ in the (n+1)th cycle is set to be the same as the target stop position $X^{[L]}{}_0(n)$ in the nth cycle.

When the actual stop position $X^{[L]}{}_1(n)$ in the nth cycle is farther than the designed target stop position $X^{[L]}{}_{00}$, the target stop position $X^{[L]}{}_0(n+1)$ in the (n+1)th cycle is set to be closer than the target stop position $X^{[L]}{}_0(n)$ in the nth cycle.

For example, when the difference $\Delta X^{[L]}(n)$ in the nth cycle is −7 mm, the correction term $k^{[L]}(n)$ is determined to be +5 mm based on the table. In this case, the target stop position $X^{[L]}{}_0(n+1)$ of the sample in the (n+1)th cycle is set to be a value obtained by adding +5 mm to the target stop position $X^{[L]}{}_0(n)$ of the sample in the nth cycle. For example, when the difference $\Delta X^{[L]}(n)$ in the nth cycle is −2 mm, the correction term $k^{[L]}(n)$ is determined to be 0 mm based on the table. In this case, the target stop position $X^{[L]}{}_0(n+1)$ of the sample in the (n+1)th cycle is set to be a value that is the same as the target stop position $X^{[L]}{}_0(n)$ of the sample in the nth cycle.

In the above description, by adding the correction term $k^{[L]}(n)$ to the target stop position $X^{[L]}{}_0(n)$ of the sample in the nth cycle, the target stop position $X^{[L]}{}_0(n+1)$ of the sample in the (n+1)th cycle is obtained. However, the method of setting the target stop position $X^{[L]}{}_0(n+1)$ of the sample in the (n+1)th cycle is not limited to this method. In addition to the known control method such as PID control, correction terms other than those used in adding and correction factors may be taken into consideration or combined.

In the above description, the actual stop position $X^{[L]}{}_1(n)$ of the sample is used to determine the correction term $k^{[L]}(n)$. However, when actually using the reaction processor 30, how to obtain the actual stop position $X^{[L]}{}_1(n)$ of the sample is a problem. This is because sensors for position detection are not disposed in each temperature region in the reaction processor 30. Thus, a method for estimating the actual stop position of the sample in each temperature region will be described.

The actual stop position $X^{[L]}_1(n)$ of the sample in the low temperature region in the nth cycle can be estimated by the following equation (4). When the estimated stop position of the sample is written as $X^{[L]}_{11}(n)$, the following is established.

$$X^{[L]}_{11}(n) = L/t^{L \to H}_p(n) * \{t^{L \to H}_{mp}(n) - t_c\} \tag{4}$$

In the equation (4), $t^{L \to H}_p(n)$ is the transit time of the sample through the fluorescence detection region 65 with regard to the movement from the low temperature region to the high temperature region in the nth cycle. Further, $t^{L \to H}_{mp}(n)$ is the time required from when the operation of the liquid feeding system 37 is started in order to move the sample until when the CPU 36 recognizes that the head of the sample has reached the fluorescence detection region 65 with regard to the movement from the low temperature region to the high temperature region in the nth cycle.

Figure 9:
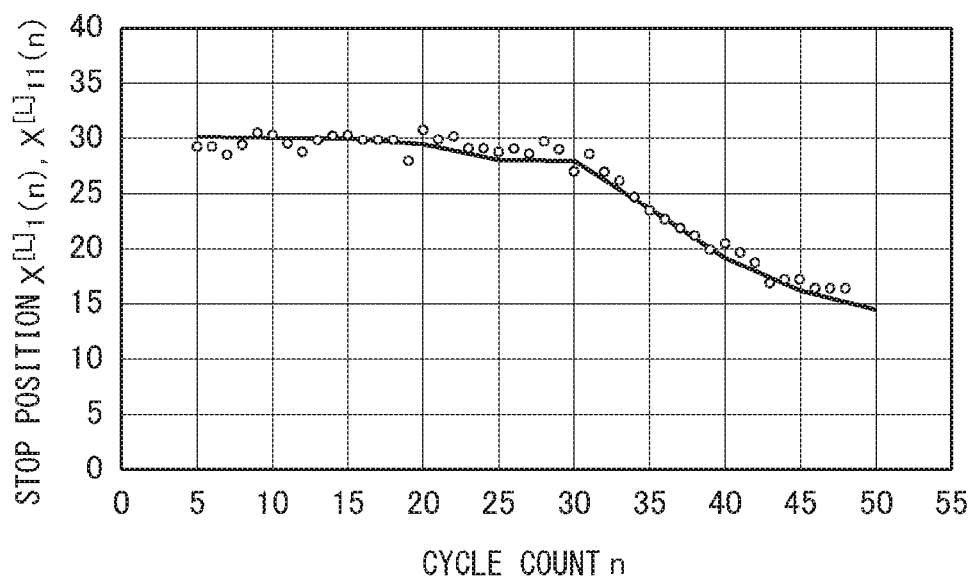
FIG. 9 is a diagram comparing, for the sample used in the experiment shown in FIG. 5, the actual stop position of the sample with a stop position estimated based on the present invention.
Figure 10:
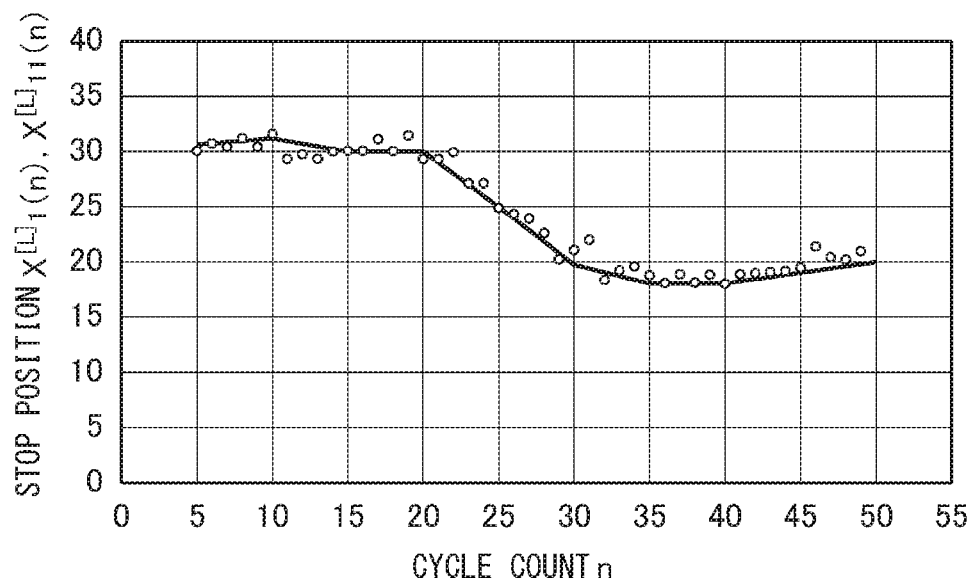
FIG. 10 is a diagram comparing, for the sample used in the experiment shown in FIG. 6, the actual stop position of the sample with a stop position estimated based on the present invention.
Figure 11:
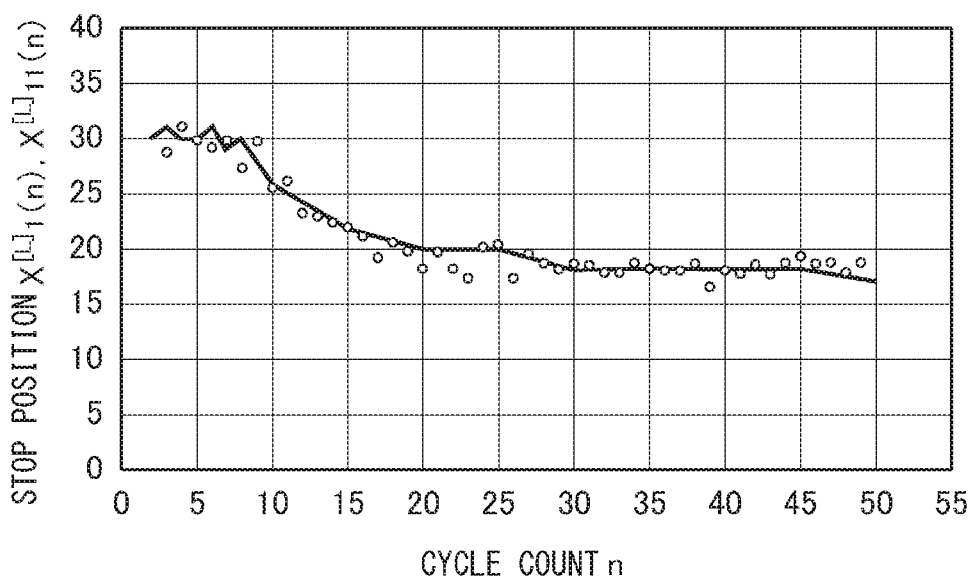
FIG. 11 is a diagram comparing, for the sample used in the experiment shown in FIG. 7, the actual stop position of the sample with a stop position estimated based on the present invention.

FIGS. 9 to 11 show the results of verifying the validity of the above equation (4). In FIGS. 9 to 11, the horizontal axis represents the cycle count n and the vertical axis represents the actual stop position $X^{[L]}_1(n)$ (measured value) of the sample and the estimated stop position $X^{[L]}_{11}(n)$ (estimated value) of the sample in the low temperature region when moving from the high temperature region to the low temperature region. In FIGS. 9 to 11, the solid line shows the measured value $X^{[L]}_1(n)$, and a o marker shows the estimated value $X^{[L]}_{11}(n)$ estimated based on the equation (4). FIG. 9 is the experimental result for the sample used in the experiment shown in the above FIG. 5. FIG. 10 is the experimental result for the sample used in the experiment shown in the above FIG. 6. FIG. 11 is the experimental result for the sample used in the experiment shown in the above FIG. 7.

From FIGS. 9 to 11, it can be determined that the measured value $X^{[L]}_1(n)$ and the estimated value $X^{[L]}_{11}(n)$ are almost equal (the absolute value of the difference therebetween is 3 mm at most). Thus, the estimation of the stop position based on the equation (4) seems to be almost accurate, and it can be found that $X^{[L]}_1(n)$ and $X^{[L]}_{11}(n)$ may be considered to be approximately equal to each other.

As explained above, the reaction processor according to the present embodiment performs movement control, which is what is called a type of feedback control, on the sample after obtaining the target stop position $X^{[L]}_0(n+1)$ of the sample with regard to the movement from the high temperature region to the low temperature region in the (n+1)th cycle based on the transit time $t^{H \to L}_p(n)$ of the sample through the fluorescence detection region 65, the (estimated) stop position $X^{[L]}_{11}(n)$ of the sample, and the target stop position $X^{[L]}_0(n)$ of the sample with regard to the movement from the high temperature region to the low temperature region in the nth cycle. The movement of the sample from the high temperature region to the low temperature region has mainly been explained above. However, the same can be applied to the movement of the sample from the low temperature region to the high temperature region as long as replacement of changing the suffixes [L], H→L, and L→H in the equations (2) through (4) to [H], L→H, and H→L, respectively, is employed.

Figure 12:
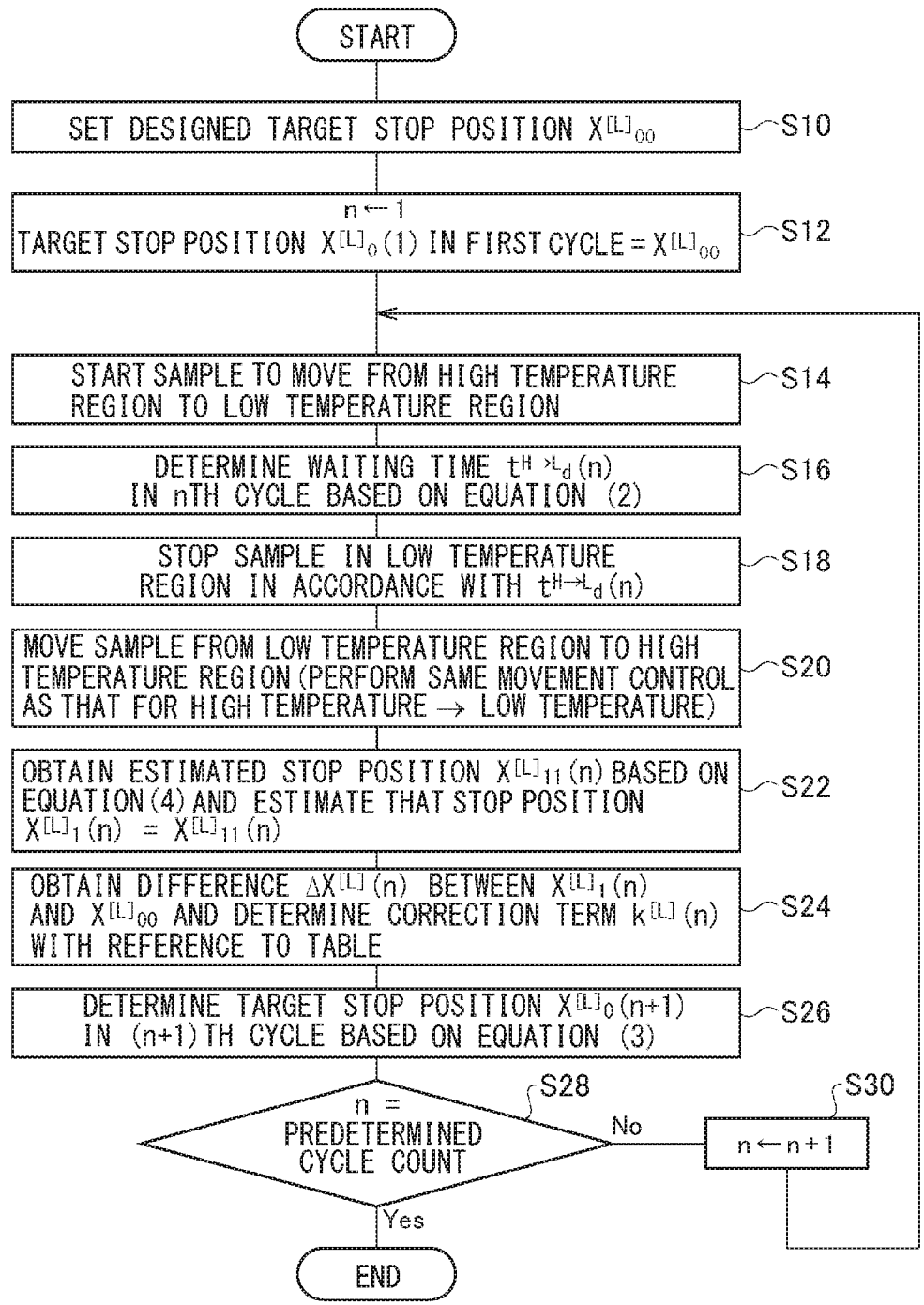
FIG. 12 is a diagram showing a flowchart for explaining a method of controlling the movement of a sample in the reaction processor according to the embodiment of the present invention.

FIG. 12 is a flowchart for explaining a method of controlling the movement of a sample in the reaction processor according to the embodiment of the present invention. In this flowchart, a control method relating to the movement of the sample from a high temperature region to a low temperature region will be explained. However, the same also applies to the movement of the sample from a low temperature region to a high temperature region.

First, in design, the CPU 36 sets the designed target stop position $X^{[L]}_{00}$, which is a position where the sample should be present in the low temperature region (S10). $X^{[L]}_{00}$ is represented by a distance from the center of the fluorescence detection region 65 and is set to be, for example, $X^{[L]}_{00}=30$ mm.

Subsequently, the CPU 36 sets the value of n to 1 and sets the target stop position $X^{[L]}_0(1)$ in the first cycle to the designed target stop position $X^{[L]}_{00}$ (S 12).

The CPU 36 operates, in the liquid feeding system 37, the first pump 39 so as to start the sample to move from the high temperature region to the low temperature region (S14). The sample passes the fluorescence detection region 65, and the CPU 36 measures the fluorescence signal intensity so as to obtain $t^{H \to L}_p(1)$ based on the threshold value and calculates and determines the waiting time $t^{H \to L}_d(1)$ in the first cycle based on the above equation (2) (S16). Regarding the threshold value for measuring $t^{H \to L}_p(1)$, estimation may be performed based on experience as an initial value when n=1 (first cycle), and the value may be determined based on the estimation. In the case of n=2 (second cycle), $t^{H \to L}_p(2)$ may be obtained based on the fluorescence signal intensity measured at the time of the movement from the high temperature region to the low temperature region when n=1 and on the threshold value. As described above, the threshold value may be 50% of the intensity difference between the intensity at the baseline and the peak intensity in the changes of the fluorescence signal intensity. Regarding the threshold value, based on the fluorescence signal intensity measured at the time of the movement from the high temperature region to the low temperature region when n=n' (n' th cycle (n' is an integer of 2 or more)), a threshold value for the movement from the high temperature region to the low temperature region for n=n'+1 ((n'+1)th cycle) and a threshold value for the movement from the low temperature region to the high temperature region for n=n'+1 ((n'+1)th cycle) may be obtained. Further, based on the fluorescence signal intensity measured at the time of the movement from the low temperature region to the high temperature region when n=n' (n' th cycle), a threshold value for the movement from the high temperature region to the low temperature region for n=n'+1 ((n'+1)th cycle) and a threshold value for the movement from the low temperature region to the high temperature region for n=n'+1 ((n'+1)th cycle) may be obtained.

At the beginning of the PCR thermal cycle using a specimen made of actual DNA or the like, the DNA etc., of the specimen has not been sufficiently amplified yet. However, even at the beginning of the thermal cycle, fluorescence is emitted from the sample containing a fluorescent probe, and it is easy to distinguish between the baseline and the peak and to obtain the threshold value based on a change in the fluorescence signal intensity that is measured. Thus, there is no problem with the measurement of $t^{H \to L}_p(n)$ and the calculation of $t^{H \to L}_d(n)$ (n is an integer of 2 or more).

Thereafter, the CPU 36 stops the sample in the low temperature region in accordance with the waiting time $t^{H \to L}_d(1)$ determined in S16 (S18). In other words, the CPU 36 instructs the liquid feeding system 37 to stop the sample at the time when the waiting time $t^{H \to L}_d(1)$ has passed since the time when the passage of the sample through the fluorescence detection region 65 is detected by the fluorescence detector 50.

After being heated for a predetermined period of time in a state of being stopped in the low temperature region, the sample moves from the low temperature region to the high temperature region (S20). Here, the same control as that for the movement from the high temperature region to the low temperature region is performed.

During the movement from the low temperature region to the high temperature region, the sample passes through the fluorescence detection region 65. After the sample passes through the fluorescence detection region 65, the CPU 36 obtains $t^{L \rightarrow H}_p(1)$ and $t^{L \rightarrow H}_{mp}(1)$, obtains an estimated stop position $X^{[L]}_{11}(1)$ of the sample in the low temperature region in the first cycle based on the above equation (4), and estimates that the actual stop position $X^{[L]}_1(1)$ is $X^{[L]}_{11}(1)$ (S22).

Next, the CPU 36 obtains the difference $\Delta X^{[L]}(1)$ between the stop position $X^{[L]}_1(1)$ of the sample in the first cycle and the designed target stop position $X^{[L]}_{00}$ and determines a correction term $k^{[L]}(1)$ with reference to a table describing the relationship between the difference $\Delta X^{[L]}(n)$ and the correction term $k^{[L]}(n)$ such as the one shown in table 1 (S24).

Subsequently, the CPU 36 determines the target stop position $X^{[L]}_0(2)$ in the second cycle based on the above equation (3) (S26).

Thereafter, the CPU 36 determines whether or not the value of n has reached a predetermined cycle count (S28). The predetermined cycle count may be determined in advance by an operator, and the number thereof is 30 to 60 cycles.

When the value of n has not reached the predetermined cycle count (No in S28), the value of n is incremented by 1 such that n=2 (S30). Thereafter, the step returns to S14, and a waiting time $t^{H \rightarrow L}_d(2)$ in the second cycle is determined based on the above equation (2) in S16. The steps S14-S26 are performed until the value of n reaches the predetermined cycle count. When the value of n reaches the predetermined cycle count (Yes in S28), the control is ended.

The above is the details of the control method when the sample 20 moves from the high temperature region to the low temperature region and stops at a predetermined position in the low temperature region. As described above, the same can be applied to the movement of the sample from the low temperature region to the high temperature region as long as replacement of changing parameters in each process, variables in each equation, and suffixes [L], H→L, and L→H to [H], L→H, and H→L, respectively, is employed.

An experiment was conducted on how the estimated stop position and the actual stop position of a sample changed with the cycle count using the sample movement control method according to the present embodiment. As in the case of Comparative Example 1 and Comparative Example 2, a sample obtained by adjusting SpeedSTAR HS DNA Polymerase was used.

Figure 13:
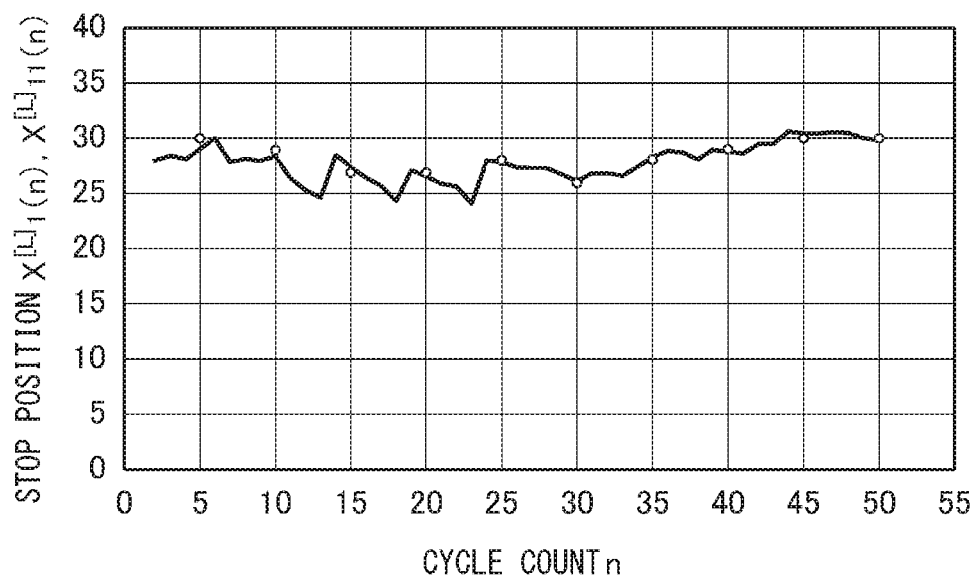
FIG. 13 is a diagram showing the result of an experiment of movement control in which the method of controlling the movement of a sample according to the present embodiment was used and is a diagram comparing the actual stop position of the sample with a stop position estimated based on the present invention in a low temperature region.

FIG. 13 shows the estimated stop position and the actual stop position in the low temperature region when the sample moves from the high temperature region to the low temperature region. The horizontal axis represents the cycle count, a o marker shows the actual stop position $X^{[L]}_1(n)$ measured every five cycles, and the solid line represents the estimated stop position $X^{[L]}_{11}(n)$ As shown in FIG. 13, good agreement was obtained between the estimated stop position and the actual stop position, and even when the cycle count reached 50, the control method according to the present embodiment was successful such that $X^{[L]}_1(n)$ in the low temperature region fell within the range of 26 mm through 30 mm and $X^{[H]}_1(n)$ of the sample in the high temperature region also fell within the range of 29.5 mm through 33.5 mm (not shown). Thus, it can be found that the sample was able to be accurately stopped at a predetermined position as compared with Comparative Examples 1 to 3 shown in FIGS. 5 to 7.

On the other hand, a path in one cycle of the sample 20 in the reaction processor 30 (two-step system) having reaction regions composed of temperature regions of two levels explained here is as follows:

(a) high temperature region (H)→(b) fluorescence detection region (fluorescence detector)→(c) low temperature region (L)→(d) fluorescence detection region (fluorescence detector)→(a) high temperature region (H)→ . . . and so on.

Note that the fluorescence detection regions (fluorescence detectors) of (b) and (d) are the same.

With regard to the basis of each element of such a path and the above-mentioned parameters, the waiting time for stopping at a predetermined position in the high temperature region (H) is calculated based on a fluorescence signal from the above fluorescence detector in (d) immediately before the sample reaches the high temperature region (H), and the estimated stop position in the high temperature region (H) is calculated based on a fluorescence signal from the above fluorescence detector in (b) immediately after the sample leaves the high temperature region (H).

The waiting time for stopping at a predetermined position in the low temperature region (L) is calculated based on a fluorescence signal from the above fluorescence detector in (b) immediately before the sample reaches the low temperature region (L), and the estimated stop position in the low temperature region (L) is calculated based on a fluorescence signal from the above fluorescence detector in (d) immediately after the sample leaves the low temperature region (L).

That is, the waiting time for stopping at a predetermined position in the high temperature region or the low temperature region is calculated based on a fluorescence signal from a fluorescence detector corresponding to a fluorescence detection region through which the sample passes immediately before reaching the region.

Further, the estimated stop position in the high temperature region or the low temperature region is calculated based on a fluorescence signal from a fluorescence detector corresponding to a fluorescence detection region through which the sample passes immediately after leaving the region. Based on this consideration, the equation (4) for obtaining the estimated stop position $X^{[L]}_{11}(n)$ of the sample in the low temperature region can be rewritten as the following equation (5).

$$X^{[L]}_{11}(n) = L/t^{L \rightarrow nt}_p(n) * \{t^{L \rightarrow nt}_{mp}(n) - t_c\} \quad (5)$$

In the equation (5), $t^{L \rightarrow nt}_p(n)$ is the transit time through a fluorescence detection region (the fluorescence detection region 65 in the case of the present embodiment) through which the sample passes immediately after leaving a low temperature region with regard to the movement from the low temperature region to the subsequent temperature region (high temperature region in the case of the present embodiment). $t^{L \rightarrow nt}_{mp}(n)$ is the time required from when the operation of the liquid feeding system 37 is started in order to move the sample until when the CPU 36 recognizes that the head of the sample has reached the fluorescence detection region (the fluorescence detection region 65) through which the sample passes immediately thereafter with regard to the movement from the low temperature region to the subsequent temperature region (the high temperature region). With regard to the estimated stop position of the sample in the high temperature region, replacement of changing the suffixes [L] and L→nt to [H] and H→nt, respectively, in the equation (5) needs to be employed. The equation (5) can be applied not only to the reaction processor 30 having the temperature regions of two levels described above but also to the reaction treatment vessel 110 having temperature regions of three levels described later.

Figure 14:
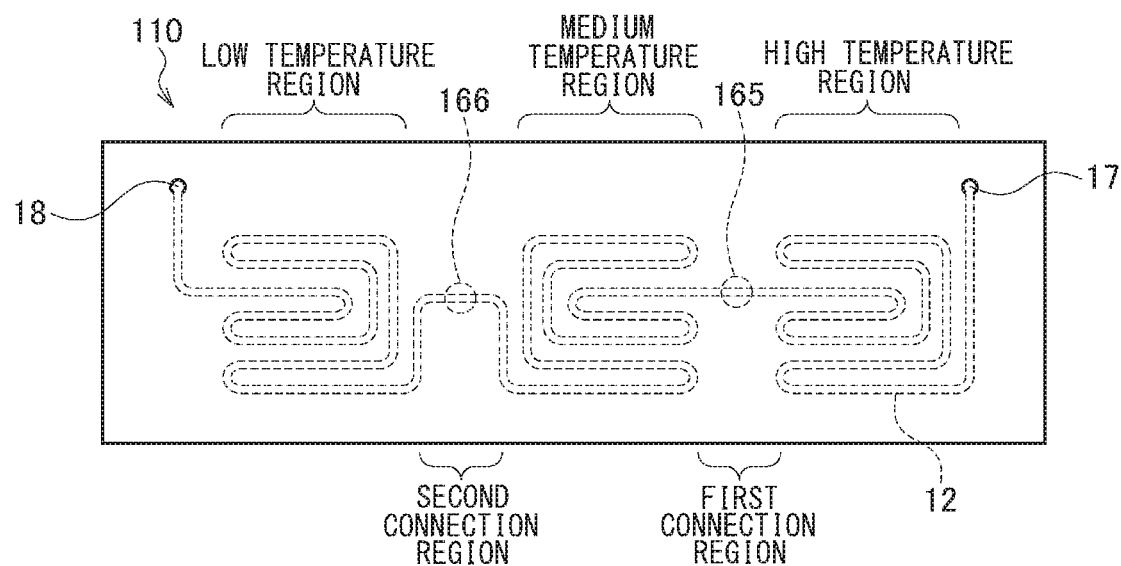
FIG. 14 is a diagram for explaining another embodiment of the reaction processing vessel.

FIG. 14 is a diagram for explaining another embodiment of the reaction processing vessel. The reaction processing vessel 10 shown in FIGS. 1A and 1B applies a thermal cycle to a sample by continuously reciprocating the sample between temperature regions of two levels: a high temperature region of, for example, about 95° C.; and a low temperature region of, for example, about 55° C. The reaction processing vessel 110 shown in FIG. 14 applies a thermal cycle to a sample by continuously reciprocating the sample between temperature regions of three levels: a high temperature region of, for example, about 95° C.; a medium temperature region of, for example, about 65° C.; and a low temperature region of, for example, about 55° C. In this case, it is possible to perform denaturation of DNA in the high temperature region, annealing in the low temperature region, and elongation in the medium temperature region.

The channel 12 of the reaction processing vessel 110 shown in FIG. 14 has a medium temperature region between a high temperature region and a low temperature region. In the same way as in the high temperature region and the low temperature region, this channel in the medium temperature region is formed of a serpiginous shape channel with continuous turns made by combining curved portions and straight portions. The channel 12 of the reaction processing vessel 110 has a first connection region located between the high temperature region and the medium temperature region and a second connection region located between the medium temperature region and the low temperature region. The first connection region and the second connection region include linear channels. In the first connection region and the second connection region, a first fluorescence detection region 165 and a second fluorescence detection region 166 are set, respectively.

Figure 15:
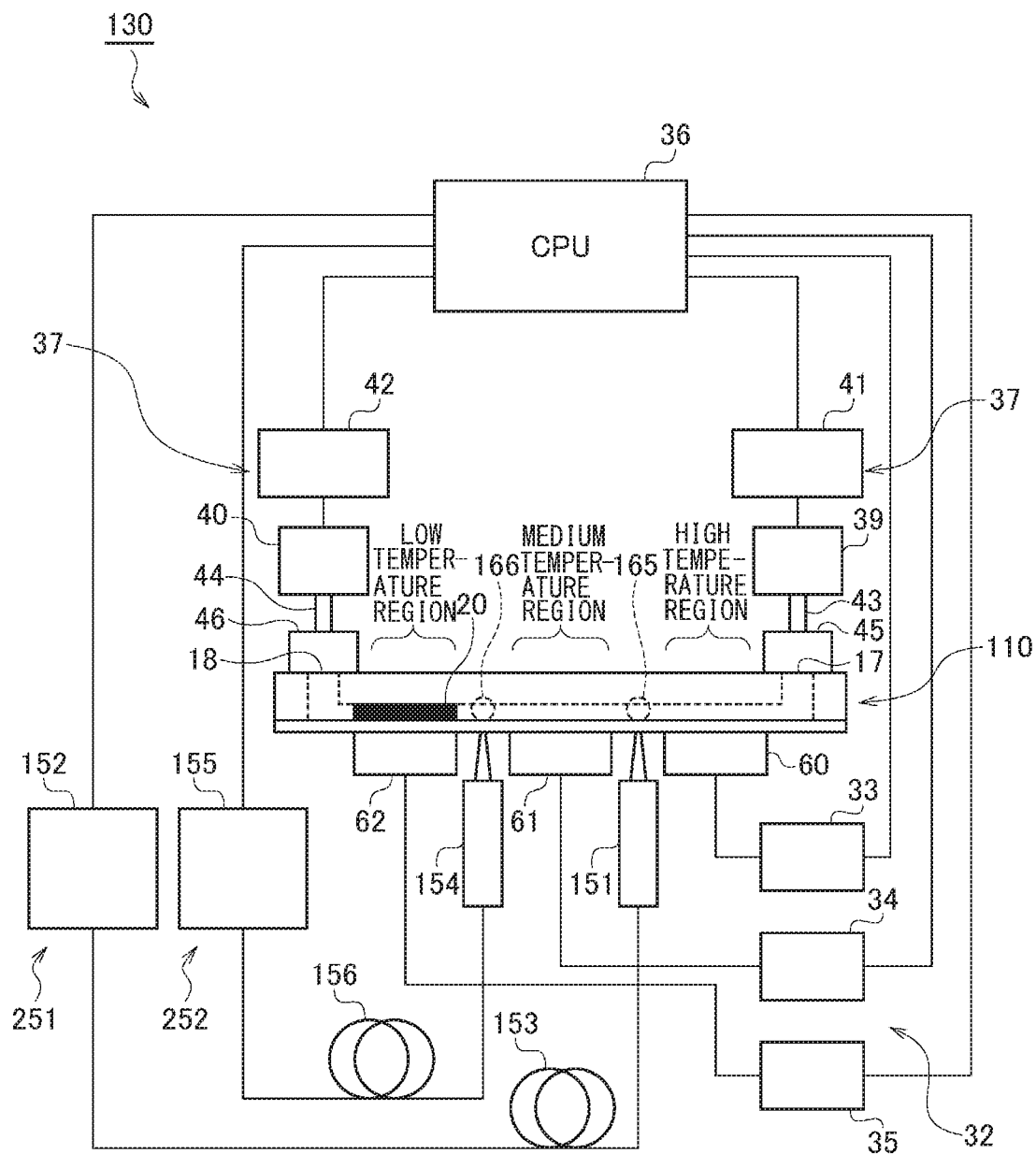
FIG. 15 is a schematic diagram for explaining another embodiment of the reaction processor.

FIG. 15 is a schematic diagram for explaining another embodiment of the reaction processor. A reaction processor 130 shown in FIG. 15 is a device for performing a thermal cycle on the reaction processing vessel 110 having temperature regions of three levels shown in FIG. 14.

In addition to a high temperature heater 60, a low temperature heater 62, a high temperature heater driver 33, and a low temperature heater driver 35, a temperature control system 32 of the reaction processor 130 further includes a medium temperature heater 61 for heating the medium temperature region of the channel 12 and a medium temperature heater driver 34 for controlling the temperature of the medium temperature heater 61.

A first fluorescence detector 251 of the reaction processor 130 includes: a first optical head 151 for detecting fluorescence from the sample 20 passing through a first fluorescence detection region 165 of the channel of the reaction processing vessel 110; a first fluorescence detector driver 152; and a first optical fiber 153 connecting the first optical head 151 and the first fluorescence detector driver 152, and a second fluorescence detector 252 includes: a second optical head 154 for detecting fluorescence from the sample 20 passing through a second fluorescence detection region 166 of the channel of the reaction processing vessel 110; a second fluorescence detector driver 155; and a second optical fiber 156 connecting the second optical head 154 and the second fluorescence detector driver 155.

To the sample 20 in the reaction processor 130, a thermal cycle is applied with a high temperature region→ a low temperature region→ a medium temperature region→ a high temperature region as one cycle. It is to be noted that in the process of the high temperature region→ the low temperature region in the reaction processor 130, the sample passes through the medium temperature region in the middle without being stopped for a predetermined time.

The operation of the sample by the reaction processor 130 will be explained in the following.

Designed target stop positions $X^{[H]}_{00}$, $X^{[M]}_{00}$, and $X^{[L]}_{00}$ in the high temperature region, the medium temperature region, and the low temperature region are predetermined. These are expressed as $X^{[H]}_{0}(1)$, $X^{[M]}_{0}(1)$, and $X^{[L]}_{0}(1)$ as initial values. Further, in the same way as in the above-described two-step system, respective threshold values required for calculating waiting times $t^{H\rightarrow L}_{d}(1)$, $t^{L\rightarrow M}_{d}(1)$, and $t^{M\rightarrow H}_{d}(1)$ for respective temperature regions are predetermined. It should be noted that the suffix M indicates the medium temperature region.

In the liquid feeding system 37, the first pump 39 is operated so as to move the sample 20 from the high temperature region (H) to the low temperature region (L). In two fluorescence detection regions located between these regions, when the sample 20 passes through the second fluorescence detection region 166 on the side close to the low temperature region, the measurement of a transit time $t^{H\rightarrow L}_{2p}(n)$ and the calculation of a waiting time $t^{H\rightarrow L}_{2d}(n)$ based on the above equation (2) are performed based on a fluorescence signal from the second fluorescence detector 252 (the suffixes 1 and 2 of the symbol t indicating time mean that the respective waiting times are obtained based on the passage through the first fluorescence detection region 165 and the passage through the second fluorescence detection region 166, respectively, and the same applies herein after). After the waiting time $t^{H\rightarrow L}_{2d}(n)$ has passed since the time at which the sample 20 passes through the second fluorescence detection region 166, the stopping of the first pump 39 is instructed, and the sample 20 is stopped inside the low temperature region.

Further, in the two fluorescence detection regions, when the sample passes through the first fluorescence detection region 165 on the side close to the high temperature region, the measurement of $t^{H\rightarrow L}_{1p}(n)$ and the calculation of $t^{H\rightarrow L}_{mp}(n)$ are performed based on a fluorescence signal from the first fluorescence detector 251, and an estimated stop position $X^{[H]}_{11}(n)$ of the sample in the high temperature region is obtained based on the above equation (4) so as to be estimated as the actual stop position $X^{[H]}_{1}(n)$. When there are two or more fluorescence detection regions between the movement regions, the calculation of the waiting time for stopping the sample is performed based on a fluorescence signal from a fluorescence detector related to a fluorescence detection region closest to a region of arrival, and the stop position in a region of departure is estimated based on a fluorescence signal from a fluorescence detector related to a fluorescence detection region closest to the region of departure.

After the sample 20 is stopped for a fixed period of time in the low temperature region, in the liquid feeding system 37, the second pump 40 is operated so as to move the sample 20 from the low temperature region (L) to the medium temperature region (M). When the sample passes through the second fluorescence detection region 166 located between these regions, the measurement of a transit time $t^{L\rightarrow M}_{2p}(n)$ and the calculation of a waiting time $t^{L\rightarrow M}_{2d}(n)$ based on the above equation (2) are performed based on a fluorescence signal from the second fluorescence detector 252. After the waiting time $t^{L\rightarrow M}_{2d}(n)$ has passed since the time at which the sample 20 passes through the second fluorescence detection region 166, the stopping of the second pump 40 is instructed, and the sample 20 is stopped inside the medium temperature region. Further, the measurement of $t^{L \to M}{}_{2p}(n)$ and the calculation of $t^{L \to M}{}_{2mp}(n)$ are performed based on the fluorescence signal, and an estimated stop position $X^{[L]}{}_{11}(n)$ of the sample 20 in the low temperature region is obtained based on the above equation (4) so as to be estimated as the actual stop position $X^{[L]}{}_{1}(n)$.

After the sample 20 is stopped for a fixed period of time in the medium temperature region, in the liquid feeding system 37, the second pump 40 is operated so as to move the sample 20 from the medium temperature region (M) to the high temperature region (H). When the sample passes through the first fluorescence detection region 165 located between these regions, the measurement of a transit time $t^{M \to H}{}_{1p}(n)$ and the calculation of a waiting time $t^{M \to H}{}_{1d}(n)$ based on the above equation (2) are performed based on a fluorescence signal from the first fluorescence detector 251. After the waiting time $t^{M \to H}{}_{1d}(n)$ has passed since the time at which the sample 20 passes through the first fluorescence detection region 165, the stopping of the second pump 40 is instructed, and the sample 20 is stopped inside the high temperature region. Further, the measurement of $t^{M \to H}{}_{1p}(n)$ and the calculation of $t^{M \to H}{}_{1mp}(n)$ are performed based on the fluorescence signal, and an estimated stop position $X^{[M]}{}_{11}(n)$ of the sample in the medium temperature region is obtained based on the above equation (4) so as to be estimated as the actual stop position $X^{[M]}{}_{1}(n)$.

On the other hand, a path in one cycle of the sample 20 in the reaction processor 130 (three-step system) having a reaction region composed of temperature regions of three levels explained here is as follows:

(a) high temperature region (H)→(b) first fluorescence detection region (first fluorescence detector)→(c) second fluorescence detection region (second fluorescence detector)→(d) low temperature region (L)→(e) second fluorescence detection region (second fluorescence detector)→(f) medium temperature region (M)→(g) first fluorescence detection region (first fluorescence detector)→(a) high temperature region (H)→ . . . and so on.

Although a medium temperature region (M) exists between (b) and (c), the region is not included in the path since the sample merely passes through the region without being stopped.

With regard to the basis of each element of such a path and the above-mentioned parameters, the waiting time for stopping at a predetermined position in the high temperature region (H) is calculated based on a fluorescence signal from the above first fluorescence detector in (g) immediately before the sample reaches the high temperature region (H). Further, the estimated stop position in the high temperature region (H) is calculated based on a fluorescence signal from the first fluorescence detector in (b) immediately after the sample leaves the high temperature region (H).

In the same way, the waiting time for stopping at a predetermined position in the medium temperature region (M) is calculated based on a fluorescence signal from the above second fluorescence detector in (e) immediately before the sample reaches the medium temperature region (M). Further, the estimated stop position in the medium temperature region (M) is calculated based on a fluorescence signal from the first fluorescence detector in (g) immediately after the sample leaves the medium temperature region (M).

Further, the waiting time for stopping at a predetermined position in the low temperature region (L) is calculated based on a fluorescence signal from the above second fluorescence detector in (c) immediately before the sample reaches the low temperature region (L). Further, the estimated stop position in the low temperature region (L) is calculated based on a fluorescence signal from the second fluorescence detector in (e) immediately after the sample leaves the low temperature region (L).

From the above, the waiting time for stopping at a predetermined position in the high temperature region, the medium temperature region, or the low temperature region is calculated based on a fluorescence signal from a fluorescence detector corresponding to a fluorescence detection region through which the sample passes immediately before reaching the region.

Further, the estimated stop position in each region is calculated based on a fluorescence signal from a fluorescence detector corresponding to a fluorescence detection region through which the sample passes immediately after leaving the region. Therefore, the above equation (5) is also applicable to the reaction processing vessel 110 having a temperature regions of three levels. Therefore, with regard to the estimated stop position of the sample in the high temperature region, replacement of changing the suffixes [L] and L→nt to [H] and H→nt, respectively, in the equation (5) needs to be employed. Further, with regard to the estimated stop position of the sample in the medium temperature region, replacement of changing the suffixes [L] and L→nt to [M] and M→nt, respectively, in the equation (5) needs to be employed.

As described above, even in the case of the reaction processor 130 (three-step system) having a reaction region composed of temperature regions of three levels, a fluorescence signal from a fluorescence detector provided immediately before or immediately after a corresponding temperature region and the position of the sample are to be taken into consideration. This is the same as in the case of the reaction processor 30 having the reaction regions composed of the temperature regions of two levels described above.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

What is claimed is:

1. A reaction processor comprising:
a reaction processing vessel in which a channel where a sample moves is formed;
a liquid feeding system that moves and stops the sample in the channel;
a temperature control system that provides a plurality of temperature regions each maintained at a different temperature, the plurality of temperature regions including at least a first temperature region and a second temperature region;
a detection system that detects the sample passing through a detection region that is set between the first temperature region and the second temperature region of the channel; and
a control unit that controls the liquid feeding system based on a signal detected by the detection system,
wherein the control unit is formed to perform reciprocation control for a plurality of cycles on the sample where, in one cycle, the sample is stopped for a fixed period of time in the first temperature region, moves from the first temperature region to the second temperature region after passing through the detection region and is then stopped for a fixed period of time, then returns to the first temperature region and then stops, wherein given that:

a waiting time required until the time at which the control unit instructs the liquid feeding system to stop the sample after the time at which the passage of the sample through the detection region is detected by the detection system with regard to movement from the first temperature region to the second temperature region in an nth cycle (n is an integer of 1 or more) is denoted as $t^{1 \to 2}_p(n)$;

a target stop position of the sample in the second temperature region in the nth cycle is denoted as $X^{[2]}_0(n)$;

the transit time of the sample through the detection region with regard to the movement from the first temperature region to the second temperature region in the nth cycle is denoted as $t^{1 \to 2}_p(n)$;

the length of the sample in the channel is denoted as L; and a fixed period of time specific to the reaction processor is denoted as $t_c$, the waiting time $t^{1 \to 2}_d(n)$ is defined by the following equation:

$$t^{1 \to 2}_d(n) = X^{[2]}_0(n) * t^{1 \to 2}_p(n)/L - t_c, \text{ and}$$

a target stop position $X^{[2]}_0(n+1)$ of the sample in the second temperature region in an (n+1)th cycle is corrected from the target stop position $X^{[2]}_0(n+1)$ of the sample in the second temperature region in the nth cycle based on a stop position $X^{[2]}_1(n)$ of the sample in the second temperature region and a designed target stop position $X^{[2]}_{00}$ in the second temperature region in the nth cycle.

2. The reaction processor according to claim 1, wherein the target stop position $X^{[2]}_0(n+1)$ of the sample in the second temperature region in the (n+1)th cycle is corrected from the target stop position $X^{[2]}_0(n)$ of the sample in the second temperature region in the nth cycle based on the difference $\Delta X^{[2]}(n)$ between the stop position $X^{[2]}_1(n)$ of the sample in the second temperature region in the nth cycle and the designed target stop position $X^{[2]}_{00}$ in the second temperature region.

3. The reaction processor according to claim 2, wherein the target stop position $X^{[2]}_0(n+1)$ of the sample in the second temperature region in the (n+1)th cycle is determined by correcting the target stop position $X^{[2]}_0(n)$ of the sample in the second temperature region in the nth cycle.

4. The reaction processor according to claim 3, wherein the target stop position $X^{[2]}_0(n+1)$ of the sample in the second temperature region in the (n+1)th cycle is set by the following equation:

$$X^2_0(n+1) = X^{[2]}_0(n) + k^{[2]}(n), \text{ and}$$

wherein a correction term $k^{[2]}(n)$ is determined based on the relationship with the difference $\Delta X^{[2]}(n)$ in the nth cycle.

5. The reaction processor according to claim 4, wherein the correction term $k^{[2]}(n)$ is determined with reference to a table describing the relationship between the difference $\Delta X^{[2]}(n)$ and the correction term $k^{[2]}(n)$ in the nth cycle.

6. The reaction processor according to claim 2, wherein the stop position $X^{[2]}_1(n)$ of the sample in the second temperature region in the nth cycle is obtained as $X^{[2]}_{11}(n)$ determined by the following equation:

$$X^{[2]}_{11}(n) = L/t^{2 \to nt}_p(n) * \{t^{2 \to nt}_{mp}(n) - t_c\},$$

where, in this equation, $t^{2 \to nt}_p(n)$ is the transit time through a detection region through which the sample passes immediately after leaving the second temperature region with regard to movement from the second temperature region to the subsequent temperature region, and wherein $t^{2 \to nt}_p(n)$ is the time required from when the operation of the liquid feeding system is started in order to move the sample until when the control unit recognizes that the head of the sample has reached the detection region through which the sample passes immediately thereafter with regard to the movement from the second temperature region to the subsequent temperature region.

* * * * *